[ US009186041B2 ]

United States Patent
Kasumi et al.

(10) Patent No.: US 9,186,041 B2
(45) Date of Patent: Nov. 17, 2015

(54) MEDICAL INFORMATION RECORDING APPARATUS THAT DETERMINES MEDICAL SCENE OR CHANGING OF MEDICAL SCENE, SYNTHESIZES IMAGES OBTAINED BY MEDICAL EQUIPMENT, AND RECORDS SYNTHESIZED IMAGE

(71) Applicant: OLYMPUS MEDICAL SYSTEMS CORP., Tokyo (JP)

(72) Inventors: Makoto Kasumi, Hachioji (JP); Shusuke Tsuchiya, Akishima (JP); Kuniaki Kami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/922,768

(22) Filed: Jun. 20, 2013

(65) Prior Publication Data

US 2013/0342668 A1    Dec. 26, 2013

Related U.S. Application Data

(63) Continuation of application No. PCT/JP2013/050961, filed on Jan. 18, 2013.

(30) Foreign Application Priority Data

Jan. 26, 2012  (JP) ................................. 2012-014269

(51) Int. Cl.
*A61B 1/04*     (2006.01)
*A61B 1/00*     (2006.01)
(Continued)

(52) U.S. Cl.
CPC ............. *A61B 1/0002* (2013.01); *A61B 1/0005* (2013.01); *A61B 1/00009* (2013.01);
(Continued)

(58) Field of Classification Search
CPC ....................................................... A61B 1/04
USPC ......................................................... 348/74
See application file for complete search history.

(56) References Cited

U.S. PATENT DOCUMENTS 5,805,148 A * 9/1998 Swamy et al. ................. 345/547
6,184,922 B1 * 2/2001 Saito et al. ....................... 348/65
(Continued)

FOREIGN PATENT DOCUMENTS

EP         0 655 710 A2    5/1995
EP         1 870 827 A1   12/2007
(Continued)

OTHER PUBLICATIONS

International Search Report issued in Application No. PCT/JP2013/050961; Dated Feb. 19, 2013 (With Translation).
(Continued)

*Primary Examiner* — Jay Patel
*Assistant Examiner* — Francis G Geroleo
(74) *Attorney, Agent, or Firm* — Oliff PLC

(57) ABSTRACT

A medical information recording apparatus includes: an input portion that includes a plurality of input terminals and into which a medical image can be inputted from a plurality of image pickup apparatuses, and that detects whether the medical image is inputted through any input terminal among the plurality of input terminals and outputs a detection result; a screen synthesis portion that performs synthesis processing according to one synthesis pattern among a predefined plurality of synthesis patterns for one or more of the medical images inputted through the plurality of input terminals, determines a medical scene or changing of the medical scene based on a detection result of the input portion, switches the synthesis pattern based on a determination result, and outputs a synthesized image based on the one or more medical images that are inputted; and a recording processing portion that records the synthesized image as a single image file.

4 Claims, 17 Drawing Sheets

(51) Int. Cl.
*H04N 5/77* (2006.01)
*H04N 9/82* (2006.01)
*H04N 5/262* (2006.01)
*A61B 8/08* (2006.01)
*A61B 8/00* (2006.01)
*H04N 5/91* (2006.01)
*A61B 5/0402* (2006.01)
*A61B 6/12* (2006.01)
*A61B 6/00* (2006.01)

(52) U.S. Cl.
CPC ............. *A61B8/0841* (2013.01); *A61B 8/5246* (2013.01); *A61B 8/585* (2013.01); *H04N 5/2624* (2013.01); *H04N 5/772* (2013.01); *H04N 9/8205* (2013.01); *A61B 5/0402* (2013.01); *A61B 6/12* (2013.01); *A61B 6/463* (2013.01); *H04N 5/91* (2013.01)

(56) References Cited

U.S. PATENT DOCUMENTS

| | | | |
|---|---|---|---|
| 6,636,254 B1 | 10/2003 | Onishi et al. | |
| 7,206,029 B2 | 4/2007 | Cohen-Solal | |
| 7,304,662 B1 * | 12/2007 | Sullivan et al. | 348/150 |
| 8,328,712 B2 * | 12/2012 | Nishiyama et al. | 600/109 |
| 2001/0002842 A1 * | 6/2001 | Ozawa | 348/45 |
| 2008/0122924 A1 | 5/2008 | Tashiro | |
| 2009/0030306 A1 * | 1/2009 | Miyoshi et al. | 600/424 |
| 2010/0087709 A1 * | 4/2010 | Bertolero et al. | 600/116 |

FOREIGN PATENT DOCUMENTS

| | | |
|---|---|---|
| JP | A-08-018861 | 1/1996 |
| JP | A-2008-000282 | 1/2008 |
| JP | A-2009-039243 | 2/2009 |
| JP | 2011/130793 A | 7/2011 |
| WO | WO 2011/152489 A1 | 12/2011 |

OTHER PUBLICATIONS

Jan. 1, 2011, N-Cast Corporation, "Presentation Recorder PR-720-P," NCast Take Streaming Further, www.ncast.com, http://www.ncast.com/pdf/NCast-DS-PR720P.pdf, retrieved on Jun. 22, 2015.

Jun. 30, 2015 Supplemental European Search Report issued in EP 13 74 1490.

* cited by examiner (a)  (b)

FIG.14
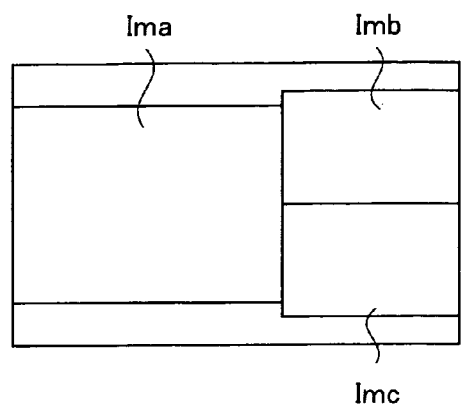
(a)
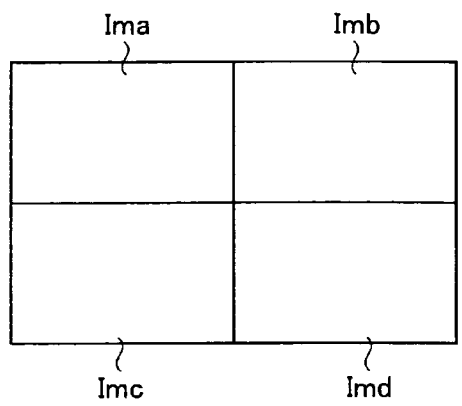
(b)

FIG. 16
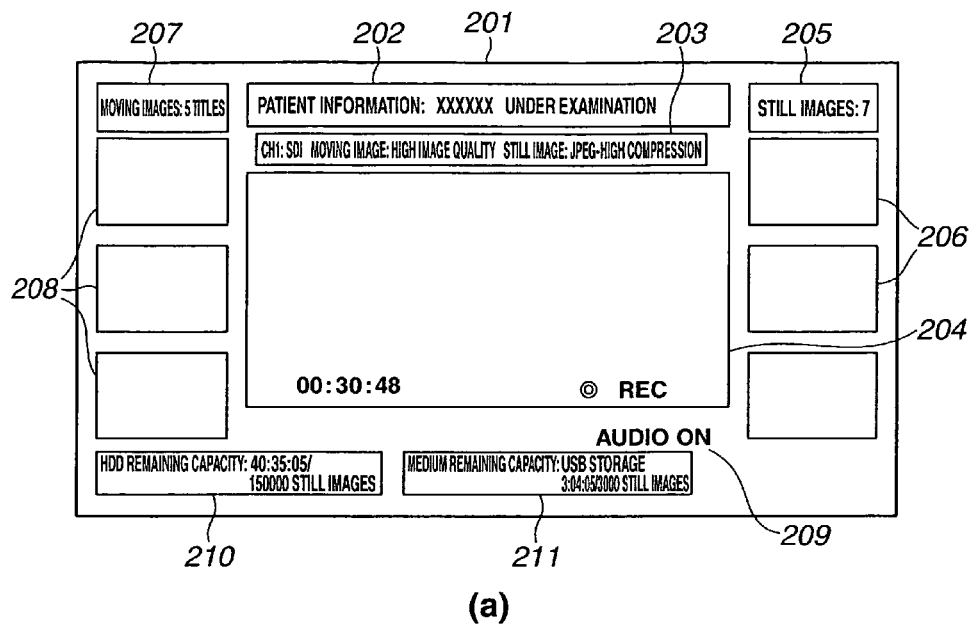
(a)
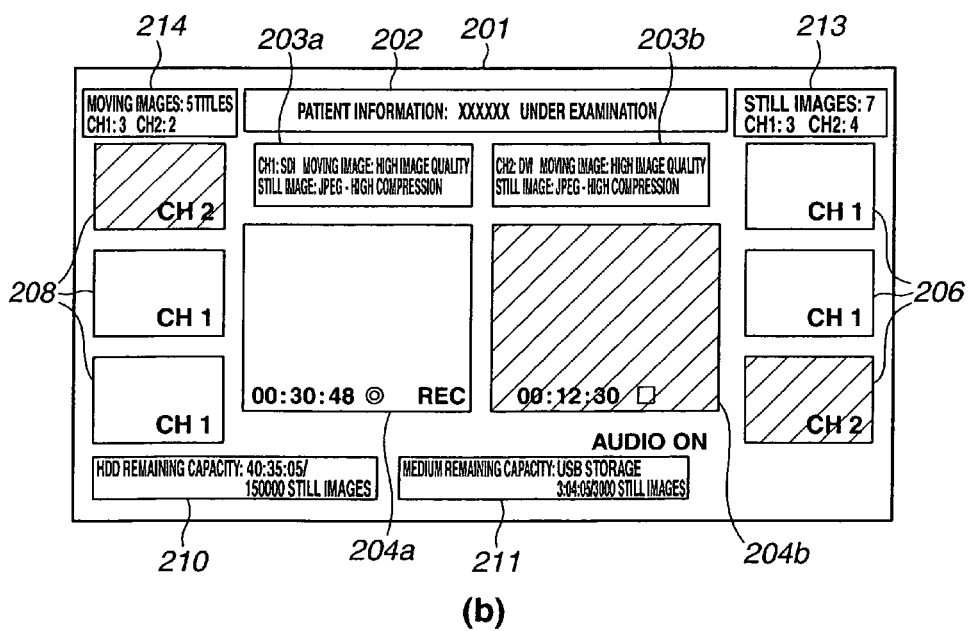
(b)

FIG.19

| | INTERNAL HDD MANAGEMENT TABLE | | | | | EXTERNAL MEDIA MANAGEMENT TABLE | |
|---|---|---|---|---|---|---|---|
| No. | ID | PATIENT NAME | DATE | FILE MANAGEMENT No. | FLAG | WRITE MEDIUM TYPE | SERIAL No. OF MEDIUM |
| 1 | 1234567 | K.J | 2010/02/16 14:26 | h-1234567-1 | 1 | BD | VOLUME LABEL: IMH-20 |
| 2 | 1234567 | K.J | 2010/02/16 14:26 | h-1234567-2 | 1 | BD | VOLUME LABEL: IMH-20 |
| 3 | 1234567 | K.J | 2010/02/16 14:26 | h-1234567-3 | 1 | BD | VOLUME LABEL: IMH-20 |
| 4 | 2234567 | M.N | 2010/06/22 08:32 | h-2234567-1 | 0 | USB | j-87678t5e |
| 5 | 2234567 | M.N | 2010/06/22 08:32 | h-2234567-2 | 0 | USB | j-87678t5e |
| 6 | 5234332 | K.J | 2010/02/16 14:26 | h-5234332-1 | 1 | BD | VOLUME LABEL: IMH-20 |
| 7 | 9987654 | J.J | 2010/08/09 10:45 | h-9987654-1 | 1 | PC-18682 | F-1298734 |

MEDICAL INFORMATION RECORDING APPARATUS THAT DETERMINES MEDICAL SCENE OR CHANGING OF MEDICAL SCENE, SYNTHESIZES IMAGES OBTAINED BY MEDICAL EQUIPMENT, AND RECORDS SYNTHESIZED IMAGE

CROSS REFERENCE TO RELATED APPLICATION

This application is a continuation application of PCT/JP2013/050961 filed on Jan. 18, 2013 and claims benefit of Japanese Application No. 2012-014269 filed in Japan on Jan. 26, 2012, the entire contents of which are incorporated herein by this reference.

BACKGROUND OF THE INVENTION

1. Field of the Invention

The present invention relates to a medical information recording apparatus that records an image that is obtained by a medical apparatus such as an endoscope.

2. Description of the Related Art

Endoscopes are already in widespread use in medical fields and the like. Medical images obtained by endoscopes are recorded on various kinds of media to record diagnoses and cases. In recent years, accompanying increases in the capacity of recording media, recording of moving images from endoscopes has been also being performed. For example, an apparatus has been disclosed that performs image recording processing in accordance with image processing. In some cases, such recording processing of medical images is digitized and the medical images are stored in a computer-readable file format.

In this connection, in medical institutions, a large number of modalities such as endoscopes, X-rays, and ultrasound diagnostic apparatuses and the like are combined and endoscopic images, ultrasound images, and X-ray images are recorded, and furthermore, a variety of images (hereunder, referred to as "medical images") such as an image showing the state of a surgeon's hands and an image showing the situation within the room or the like are sometimes recorded. In this case, it is also possible to synthesize a plurality of medical images that are recorded to thereby record the images as a single medical image (for example, see Japanese Patent Application Laid-Open Publication No. 2009-039243). For example, during endoscopic treatment, in a case where an endoscopic image and an image showing the state of a surgeon's hands are simultaneously recorded as a synthesized image in synchrony with each other, the synthesized image is extremely useful as educational material for young doctors since it is possible to ascertain at a single glance a method by which the endoscope is caused to approach a lesioned part to accurately capture an image thereof as well as the appearance of the actual endoscopic image.

A recording apparatus has a plurality of input connectors, and can obtain a required synthesized image during recording by connecting the required modalities to the respective connectors. However, in comparatively small-scale hospitals and the like, in many cases a recording apparatus or the like is moved frequently, and there are also many cases where it is necessary to connect the respective modalities and the recording apparatus before recording. In addition, to record a synthesized image it is necessary to specify the connectors to which the images to be synthesized are to be inputted and to also perform setting operations for generating a synthesized image. Consequently, relatively complicated operations must be performed in order to record a synthesized image of medical images.

In this connection, depending on the contents of the medical action, it is conceivable that not only the kinds of medical images to be recorded will be different, but also that the kinds of medical images to be recorded may differ during the course of the medical action. For example, it is conceivable that a case may arise in which one medical image among medical images from two modalities is recorded for the entire duration of the medical action, while the other medical image among the medical images from the two modalities is recorded during only part of the duration of the medical action or the like. More specifically, in some cases recording of an endoscopic image that captures an image of a surface layer of a lesioned part continues at all times, while an ultrasound image from an ultrasound diagnostic apparatus that is temporarily used for diagnosing the invasion depth of the lesioned part is only recorded at that particular time.

SUMMARY OF THE INVENTION

A medical information recording apparatus according to one aspect of the present invention includes: an input portion that has a plurality of input terminals and into which a medical image can be inputted from a plurality of image pickup apparatuses, and that detects whether the medical image is inputted through any input terminal among the plurality of input terminals and outputs a detection result; a screen synthesis portion that performs synthesis processing in accordance with one synthesis pattern among a predefined plurality of synthesis patterns with respect to one or more of the medical images inputted through the plurality of input terminals, determines a medical scene or changing of the medical scene based on a detection result of the input portion, switches the synthesis pattern based on a determination result, and outputs a synthesized image that is based on the one or more medical images that are inputted; and a recording processing portion that records the synthesized image as a single image file.

A medical information recording apparatus according to another aspect of the present invention includes: an input portion that has a plurality of input terminals and into which a medical image can be inputted from a plurality of image pickup apparatuses, and that detects whether the medical image is inputted through any input terminal among the plurality of input terminals and outputs a detection result; a screen synthesis portion that performs synthesis processing in accordance with one synthesis pattern among a predefined plurality of synthesis patterns with respect to one or more of the medical images inputted through the plurality of input terminals, determines a medical scene or changing of the medical scene based on a detection result of the input portion and an image analysis result with respect to one or more of the medical images inputted through the plurality of input terminals, switches the synthesis pattern based on a determination result, and outputs a synthesized image that is based on the one or more medical images that are inputted; and a recording processing portion that records the synthesized image as a single image file.

BRIEF DESCRIPTION OF THE DRAWINGS

FIG. 14 is an explanatory view for describing synthesis patterns according to the second modification;

FIG. 16 is an explanatory view illustrating display examples of a second display mode;

FIG. 19 is an explanatory view illustrating a management table as an example of management information that is recorded as a database 31*a*.

DETAILED DESCRIPTION OF THE PREFERRED EMBODIMENTS

Figure 1:
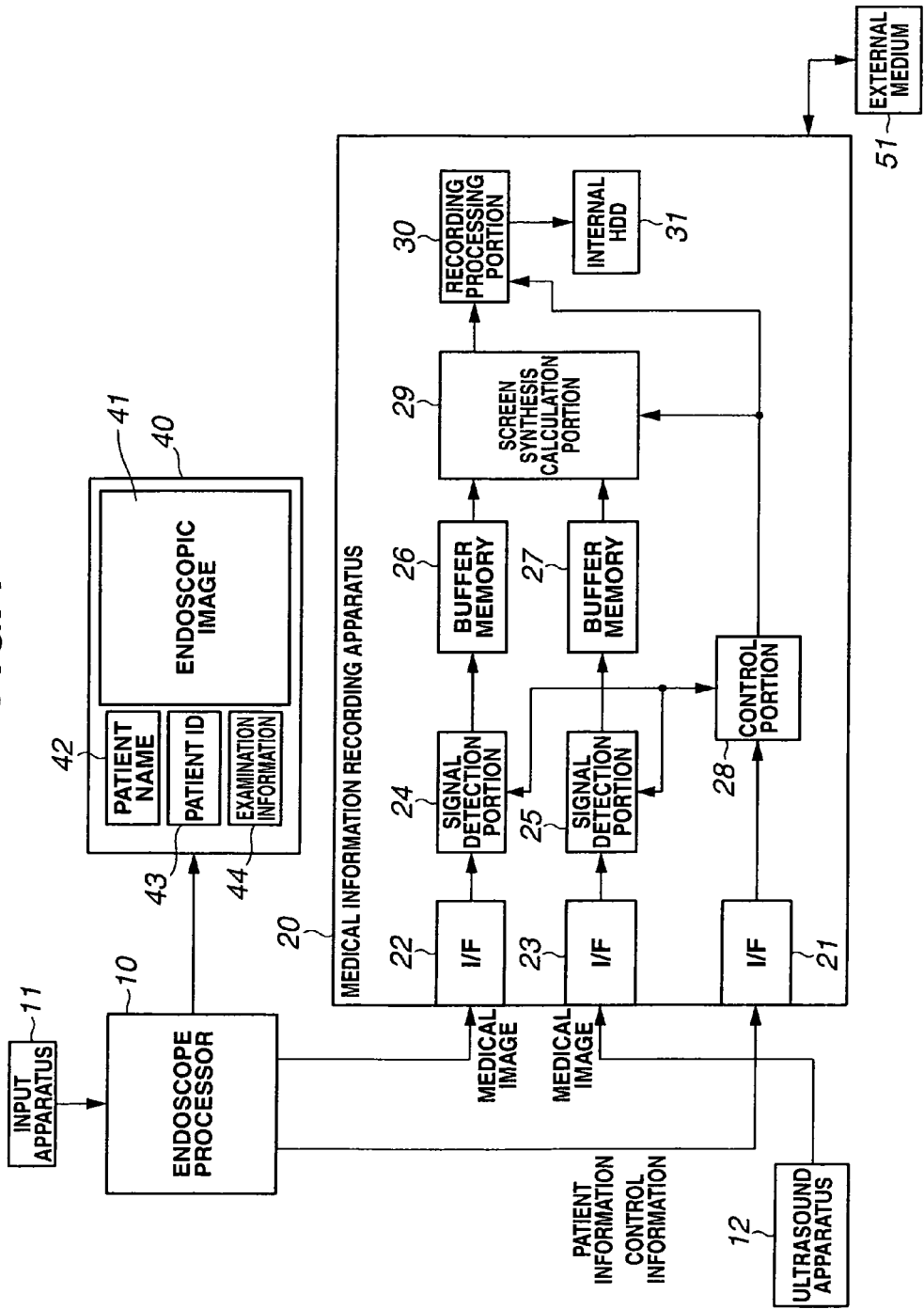
FIG. 1 is a block diagram illustrating a medical information recording system in which a medical information recording apparatus according to a first embodiment of the present invention is incorporated.

Hereunder, embodiments of the present invention are described in detail with reference to the drawings.
(First Embodiment)
FIG. 1 is a block diagram illustrating a medical information recording system in which a medical information recording apparatus according to a first embodiment of the present invention is incorporated.

The present embodiment will be described with respect to a case in which an endoscope processor 10 and an ultrasound apparatus 12 are used as apparatuses that output medical information. The endoscope processor 10 can take in an image from an unshown endoscope or the like and perform image signal processing thereon to generate a medical image such as an endoscopic image. A medical image from the endoscope processor 10 is supplied to a medical information recording apparatus 20 and a monitor 40. The ultrasound apparatus 12 generates a medical image such as an ultrasound image and outputs the medical image to the medical information recording apparatus 20.

An input apparatus 11 is constituted by an unshown keyboard or buttons, switches (not shown) or the like that are provided on the body of the endoscope processor 10, and is configured to enable performance of an operation to input an instruction for image processing of the endoscope processor 10 or an operation to input patient information or the like. The endoscope processor 10 can output the patient information to the medical information recording apparatus 20.

The endoscope processor 10 also generates control information for controlling the medical information recording apparatus 20. Examples of the control information include image recording start information that instructs the start of recording of a medical image that is a moving image, image recording end information that instructs the end of the recording, still image recording information that instructs recording of a medical image that is a still image, and examination end information that instructs the end of an examination. For example, the endoscope processor 10 is configured so that image processing is controlled in response to various types of scope operations such as operation of a release button or an image recording start button provided on the endoscope, and to be able to generate control information according to the various types of scope operations and output the control information to the medical information recording apparatus 20.

Furthermore, the endoscope processor 10 can superimpose patient information on a medical image generated based on an output of the endoscope or the like, and output the medical image. In such case, the endoscope processor 10 can also generate a medical image including a display region based on the patient information and a display region based on the endoscopic image.

The monitor 40 can display a medical image from the endoscope processor 10 on a screen. In the example in FIG. 1, an endoscopic image, a patient name, a patient ID, and examination information are displayed in a region 41 on the right side and regions 42 to 44 on the left side of the screen of the monitor 40, respectively.

The medical information recording apparatus 20 includes an interface (hereinafter referred to as "I/F") 21 through which information is exchanged with the endoscope processor 10, an I/F 22 through which a medical image from the endoscope processor 10 is taken in, and an I/F 23 through which a medical image from the ultrasound apparatus 12 is taken in. The I/F 21 is, for example, an interface based on the RS-232C standard, and takes in patient information and control information from the endoscope processor 10. The I/F 22 and I/F 23 are interfaces suitable for image transmission, and take in medical images from various modalities.

Note that although FIG. 1 illustrates an example in which only interfaces of two systems are shown and the endoscope processor 10 and the ultrasound apparatus 12 are connected to the respective interfaces, the medical information recording apparatus 20 may have interfaces of three systems or more. It is also possible for each interface to be equipped with a plurality of input terminals. For example, a plurality of kinds of terminals can be employed as input terminals, such as a DVI (digital visual interface) terminal, an SDI (serial digital interface) terminal, an RGB terminal, a Y/C terminal and a VIDEO terminal. Apart from an endoscope processor and an ultrasound apparatus, for example, an operative field camera, an X-ray observation apparatus, or an endoscope processor other than the endoscope processor 10 can be connected to the input terminals.

The medical information recording apparatus 20 is configured to start recording of a medical image that is a moving image (hereinafter, also referred to as "original moving image") that has been taken in through the I/F 22, and thereafter end the recording, upon control information that is generated in response to an operation of the image recording start button and an operation of an image recording end button that are provided on the endoscope being supplied to the medical information recording apparatus 20 through the I/F 21.

In the present embodiment, video signals that are inputted through the I/F 22 and I/F 23 are supplied to signal detection portions 24 and 25, respectively. The signal detection portions 24 and 25 are controlled by a control portion 28, and can detect whether or not a video signal was inputted through the I/F 22 and I/F 23.

Figure 2:
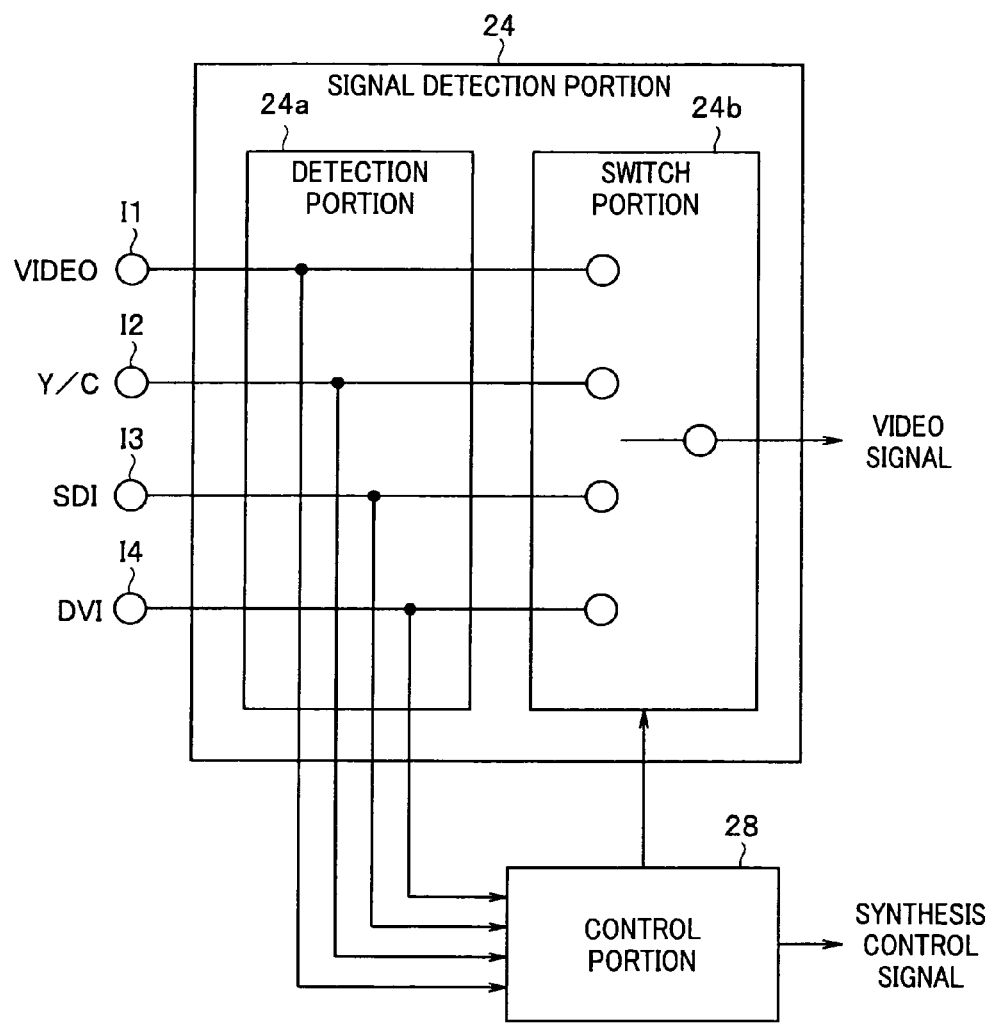
FIG. 2 is a block diagram illustrating an example of the specific configuration of signal detection portions 24 and 25 in FIG. 1.

FIG. 2 is a block diagram that illustrates an example of the specific configuration of the signal detection portions 24 and 25 in FIG. 1. Note that the signal detection portions 24 and 25 have the same configuration as each other, and only the signal detection portion 24 is illustrated in FIG. 2. The example in FIG. 2 illustrates an example in which the I/F 22 and I/F 23 include input terminals of four systems, respectively.

In FIG. 2, the output terminals of four systems of the I/F 22 are supplied to respective input terminals I1 to I4 of the signal detection portion 24. The input terminals I1 to I4 are a VIDEO terminal, a Y/C terminal, an SDI terminal, and a DVI terminal, respectively. Video signals that are inputted through the input terminals I1 to I4 are supplied to a detection portion 24a and also supplied to a switch portion 24b. The detection portion 24a is controlled by the control portion 28, and detects video signals inputted to the respective input terminals I1 to I4, and outputs a detection result to the control portion 28. Upon receiving a detection result with respect to a video signal from the signal detection portion 24, the control portion 28 controls the switch portion 24b so as to select the input terminal at which the video signal was detected and output the inputted video signal to the signal detection portion 24.

By connecting a signal connector of the endoscope processor 10 to any one of the respective input terminals of the I/F 22 and outputting a video signal from the endoscope processor 10, the control portion 28 can detect that the video signal was inputted from the endoscope processor 10 and can also cause the video signal from the endoscope processor 10 to be outputted from the switch portion 24b. Similarly, by connecting a signal connector of the ultrasound apparatus 12 to any one of the input terminals of the I/F 23 and outputting a video signal from the ultrasound apparatus 12, the control portion 28 can detect that the video signal from the ultrasound apparatus 12 was inputted and can also cause the video signal from the ultrasound apparatus 12 to be outputted from the switch portion 24b.

Thus, by means of detection results of the signal detection portions 24 and 25, the control portion 28 can determine whether or not video signals were inputted through the I/F 22 and I/F 23, respectively. Further, when these video signals are inputted to any of the different kinds of input terminals, the control portion 28 can take in the inputted video signals. That is, a surgeon can continue to perform an ongoing medical action without stopping recording during the medical action and performing an operation to change the equipment settings. The control portion 28 is configured to generate a synthesis control signal that indicates which interface among the I/F 22 and the I/F 23 a video signal is inputted from, and output the synthesis control signal to a screen synthesis calculation portion 29.

Video signals that are outputted from the signal detection portions 24 and 25 are supplied to buffer memories 26 and 27, respectively. After temporarily holding the inputted video signals, the buffer memories 26 and 27 output the video signals to the screen synthesis calculation portion 29. The screen synthesis calculation portion 29 performs predetermined video signal processing on the inputted video signals.

In the present embodiment, the screen synthesis calculation portion 29 is configured so that, when it is indicated by a synthesis control signal from the control portion 28 that a video signal was inputted from one of the I/F 22 and I/F 23, the screen synthesis calculation portion 29 can output a medical image that is based on the inputted video signal, and when it is indicated that video signals were inputted from both of the I/F 22 and I/F 23, the screen synthesis calculation portion 29 can perform screen synthesis with respect to medical images based on the inputted two kinds of video signals, and output a synthesized image. When performing screen synthesis, the screen synthesis calculation portion 29 performs the screen synthesis using a synthesis pattern that was specified by the control portion 28 from among a previously prepared plurality of synthesis patterns such as, for example, picture-in-picture (PIP) or picture-out-picture (POP) synthesis patterns, and outputs a medical image of a moving image (original moving image).

The screen synthesis calculation portion 29 outputs the generated original moving image to a recording processing portion 30. The recording processing portion 30 performs compression processing sequentially on the inputted original moving image, and supplies the compressed moving image to the internal HDD 31 to record the compressed moving image thereon. Note that, for example, the recording processing portion 30 compresses the original moving image by performing encoding processing in accordance with a predetermined encoding method such as the H.264 method. Thus, the original moving image is recorded on the internal HDD 31.

In the present embodiment, the screen synthesis calculation portion 29 is configured to control screen synthesis in accordance with a synthesis control signal from the control portion 28 even while recording is in progress. For example, in a state in which only an endoscopic image from the I/F 22 is being inputted, an original moving image based only on the endoscopic image is generated and compressed and recorded by the screen synthesis calculation portion 29. If inputting of an ultrasound image through the I/F 23 begins during the recording, the screen synthesis calculation portion 29 is controlled by a synthesis control signal from the control portion 28 to start screen synthesis of the inputted endoscopic image and ultrasound image to generated a synthesized image. The synthesized image is supplied to the recording processing portion 30 as an original moving image, and compression of the original moving image and recording processing are continued.

Further, if input of the ultrasound image through the I/F 23 stops during the recording, the screen synthesis calculation portion 29 is controlled by the synthesis control signal from the control portion 28 to generate an original moving image of only the inputted endoscopic image, and the original moving image is compressed and recording processing is continued. Note that regardless of whether or not there is a medical image which is being inputted, the recording processing continues until image recording end information is inputted to the control portion 28. Upon image recording end information being inputted to the control portion 28, the control portion 28 instructs the recording processing portion 30 to end the recording. Upon being instructed by the control portion 28 to end the recording, the recording processing portion 30 converts the moving image that is recorded on the internal HDD 31 into a file. Thus, the original moving image recorded in the period from input of the image recording start information until input of the image recording end information is recorded as a single file.

The recording processing portion 30 is configured to be also able to provide the original moving image that is recorded on the internal HDD 31 to an external medium 51 and cause the external medium 51 to record the original moving image. Note that examples of the external medium include various kinds of recording media such as an external hard disk and a semiconductor recording medium.

Figure 3:
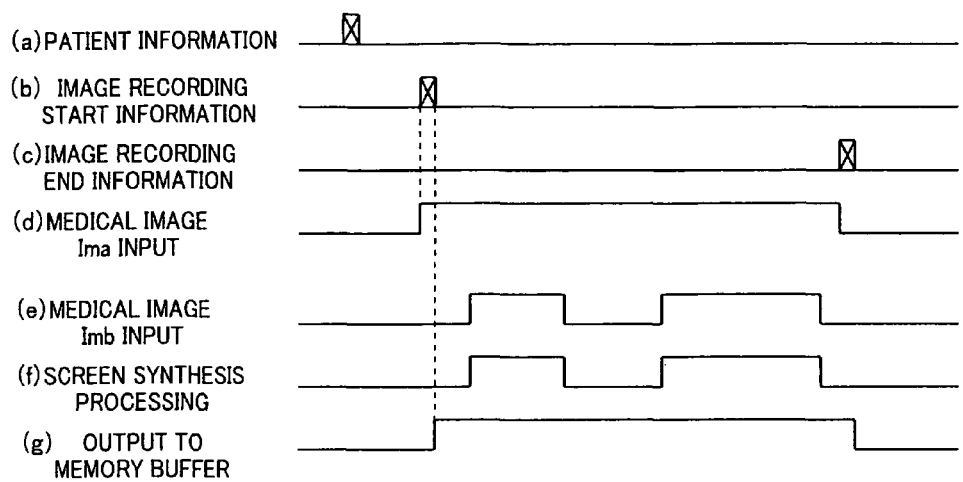
FIG. 3 is a timing chart for describing recording processing for a medical image according to the present embodiment.

FIG. 3 is a timing chart for describing recording processing for medical images according to the present embodiment, in which: FIG. 3(*a*) represents patient information; FIG. 3(*b*) represents image recording start information; FIG. 3(*c*) represents image recording end information; FIG. 3(*d*) represents input of a medical image Ima; FIG. 3(*e*) represents input of a medical image Imb; FIG. 3(*f*) represents screen synthesis processing; and FIG. 3(*g*) represents output to a memory buffer.

Upon input of patient information that is shown in FIG. 3(*a*) through the I/F 21, the control portion 28 creates folders for each item of patient information inside the internal HDD 31.

Figure 4:
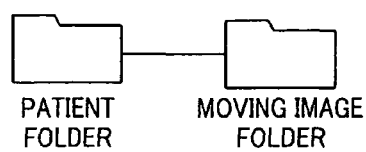
FIG. 4 is an explanatory view for describing folders that are created for each item of patient information.

FIG. 4 is an explanatory view for describing folders that are created for each item of patient information. The example in FIG. 4 shows that a patient folder is created for each patient, and furthermore that a moving image folder in which an original moving image is stored is generated as a subfolder of the patient folder.

Upon input of image recording start information that is shown in FIG. 3(*b*) through the I/F 21, the control portion 28 starts recording of an original moving image. A medical image Ima is taken in to the medical information recording apparatus 20 from the endoscope processor 10 through the I/F 22, and is supplied to the signal detection portion 24 through the I/F 22. The signal detection portion 24 detects that a video signal is inputted, and outputs the detection result to the control portion 28. As a result, the control portion 28 controls the signal detection portion 24 to cause the signal detection portion 24 to output the inputted video signal to the buffer memory 26 (FIG. 3(*g*)). The video signal is supplied from the buffer memory 26 to the screen synthesis calculation portion 29.

After subjecting the inputted video signal to predetermined signal processing, the screen synthesis calculation portion 29 compresses the medical image Ima and thereafter provides the medical image Ima to the recording processing portion 30 (FIG. 3(*f*)). The recording processing portion 30 provides the inputted medical image Ima to the internal HDD 31 to record the inputted medical image Ima. Thus, simultaneously with the input of image recording start information, recording of a medical image that is based on a video signal from the endoscope processor 10 is started.

Note that although an example in which a medical image or the like is recorded on the internal HDD 31 is described according to the present embodiment, it is clear that the external medium 51 such as an external HDD or any of various kinds of recording media can be selected as a recording destination of a medical image or the like.

In this case, it is assumed that during recording that is based on a medical image from the endoscope processor 10, the surgeon or the like turns on the power of the ultrasound apparatus 12 that is connected to the I/F 23 and causes an ultrasound image to be outputted from the ultrasound apparatus 12. The ultrasound image is supplied to the signal detection portion 25 through the 23 (FIG. 3(*e*)). The signal detection portion 25 detects that a video signal was inputted, and outputs the detection result to the control portion 28. As a result, the control portion 28 detects that a video signal has also been inputted to the I/F 23, and not just to the I/F 22, and provides the video signal that was inputted through the I/F 23 to the screen synthesis calculation portion 29 through the buffer memory 27, and also outputs a synthesis control signal for performing screen synthesis of the two inputs to the screen synthesis calculation portion 29.

The screen synthesis calculation portion 29 performs screen synthesis with respect to the inputted two medical images based on the synthesis control signal to generate a synthesized image, and continues to output the synthesized image as an original moving image. Thus, the original moving image that is inputted into the recording processing portion 30 changes from a moving image that is based on one kind of endoscopic image to a moving image of a synthesized image that is based on two kinds of images, namely, the endoscopic image and the ultrasound image. The recording processing portion 30 continues to perform compression processing and recording processing of the original moving image so that the original moving image that is being recorded on the internal HDD 31 changes from a moving image of one screen to a moving image in which two screens have been synthesized.

Recording of the original moving image that is a medical image of a moving image is continued until image recording end information is inputted as shown in FIG. 3(*c*). Upon input of the image recording end information, the control portion 28 controls the recording processing portion 30 to end the recording of the medical image. The recording processing portion 30 converts the original moving image into a file and records the file in the moving image folder for the original moving image in the patient folder created on the internal HDD 31, with an appropriate file name assigned thereto.

As described above, in the present embodiment, even if the inputted video signal changes from one kind to two kinds during recording, by merely changing from a moving image that is based on one kind of medical image to a moving image that is based on a synthesized image of two kinds of medical images without stopping the recording, a medical image (original moving image) for a moving image recording period that is specified by the image recording start information and the image recording end information is recorded on the internal HDD 31 as a single image file.

Next, operations of the embodiment configured as described above will be described with reference to the flowchart shown in FIG. 5.

Figure 5:
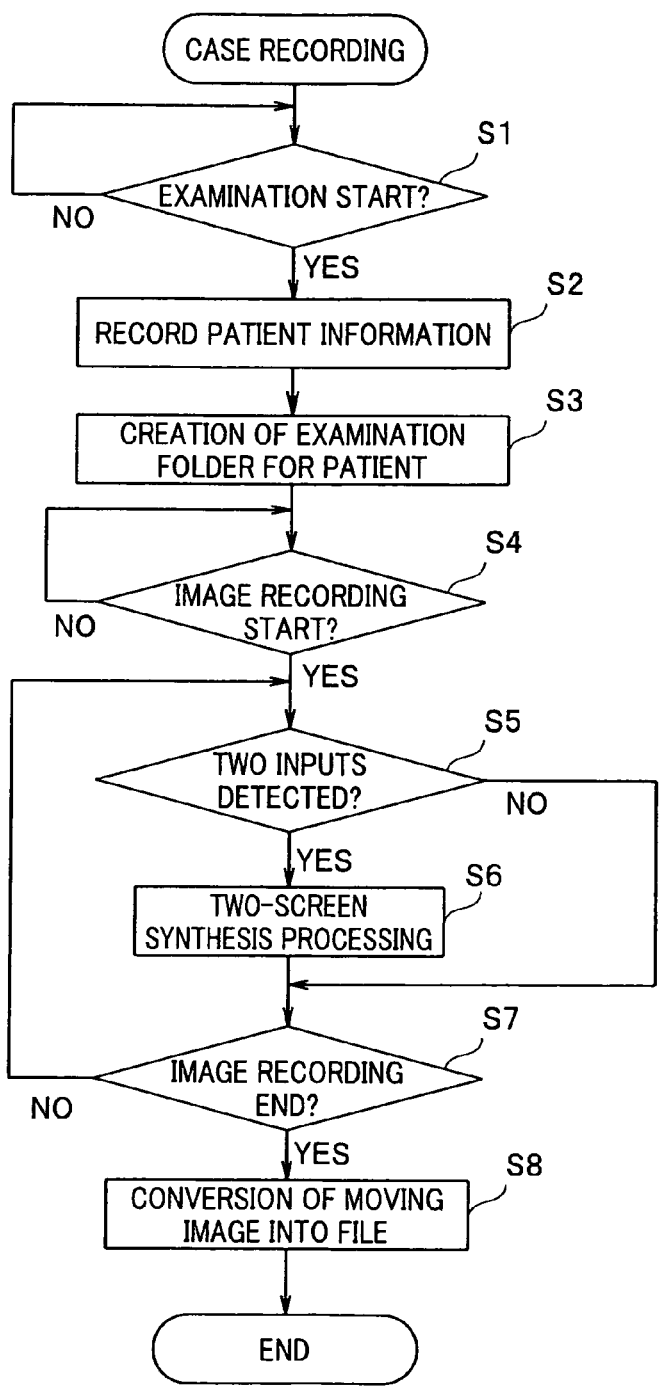
FIG. 5 is a flowchart for describing operations of the first embodiment.

In step S1 in FIG. 5, the control portion 28 determines whether or not an examination is started. For example, the control portion 28 determines that an examination is started by an operation such as input of patient information, an operation to start image recording or an operation to start an examination. It is assumed here that a surgeon operates the input apparatus 11 to input patient information. The patient information is supplied from the endoscope processor 10 to the medical information recording apparatus 20. The patient information is taken in to the control portion 28 through the I/F 21 (step S2).

The control portion 28 analyzes the inputted patient information and creates an examination folder with a folder name based on the patient information on the internal HDD 31 (step S3). For example, the control portion 28 creates an examination folder with a folder name including a patient ID. Also, the control portion 28 creates a moving image folder for original moving images in the folder.

It is assumed that the surgeon presses the image recording start button provided on an unshown endoscope or the endoscope processor 10 or the like to instruct the start of image recording. In response to this operation, the endoscope processor 10 outputs, for example, a medical image generated by superimposing the patient information onto an endoscopic image from the endoscope to the medical information recording apparatus 20, and generates image recording start information and outputs the image recording start information to the medical information recording apparatus 20. Upon receipt of the image recording start information through the I/F 21, the control portion 28 takes in a medical image that is inputted through the I/F 22. The medical image is provided to the screen synthesis calculation portion 29 through the signal detection portion 24 and the buffer memory 26, image processing is performed thereon by the screen synthesis calculation portion 29, the resulting medical image is thereafter provided to the recording processing portion 30 as an original moving image, and the recording processing portion 30 compresses the original moving image and thereafter supplies the compressed original moving image to the internal HDD 31 to start recording (step S4).

Next, in step S5, the control portion 28 determines whether or not two inputs have been detected. If a video signal from the ultrasound apparatus 12 is supplied to the I/F 23 during the recording of the original moving image, the control portion 28 determines that video signals have been inputted to both the I/F 22 and the I/F 23 by means of a detection result of the signal detection portion 25, and shifts the process to step S6 to instruct the screen synthesis calculation portion 29 to perform two-screen synthesis processing.

The video signal from the I/F 23 is provided to the screen synthesis calculation portion 29 through the signal detection portion 25 and the buffer memory 27. A synthesis control signal that instructs the performance of screen synthesis processing of two screens is sent to the screen synthesis calculation portion 29 from the control portion 28. The screen synthesis calculation portion 29 generates a synthesized image of the two inputs and outputs the resulting image as an original moving image to the recording processing portion 30. The original moving image continues to be inputted to the recording processing portion 30 before and after inputting of the video signal from the ultrasound apparatus 12, and the recording processing portion 30 continues processing with respect to input and compression of the original moving image, and supplies the compressed image to the internal HDD 31 to continue recording thereof.

Next, it is assumed that supply of the video signal from the ultrasound apparatus 12 to the I/F 23 stops during recording of the original moving image that is a synthesized image. Based on a detection result from the signal detection portion 25, the control portion 28 determines that only the video signal from the I/F 22 is being inputted, and outputs a synthesis control signal to instruct the screen synthesis calculation portion 29 to stop the two-screen synthesis processing.

As a result, the screen synthesis calculation portion 29 generates an original moving image that is based only on the endoscopic image and outputs the original moving image to the recording processing portion 30. The original moving image continues to be inputted to the recording processing portion 30 before and after inputting of the video signal from the ultrasound apparatus 12 stops, and the recording processing portion 30 continues processing with respect to input and compression of the original moving image, and supplies the compressed image to the internal HDD 31 to continue recording thereof.

In step S7, it is determined whether image recording has ended. When the surgeon presses the image recording end button, it is determined in step S7 whether or not image recording of an original moving image is in progress, and if image recording is not in progress, in step S8 the image recording processing of the original moving image ends and the original moving image is converted into a file. The original moving image file is recorded in a moving image folder for original moving images in the patient folder.

The screen synthesis processing of two inputs can be changed during recording in accordance with a detection result with respect to video signals that are inputted to the I/F 22 and the I/F 23, and during the period from the start of image recording until the end thereof, the original moving image is recorded as a single moving image file while changing between an individual image or a synthesized image in accordance with inputted signals.

Thus, according to the present embodiment, during recording of a medical image, inputting or the stopping of the inputting of a medical image that is different to the medical image that is being recorded is detected, and screen synthesis processing of the one or more medical images that are inputted is controlled based on the detection result, and it is thus possible to record an original moving image that is in accordance with changes in the inputted signals that occur even during recording as a single moving image file.

(Second Embodiment)

Figure 6:
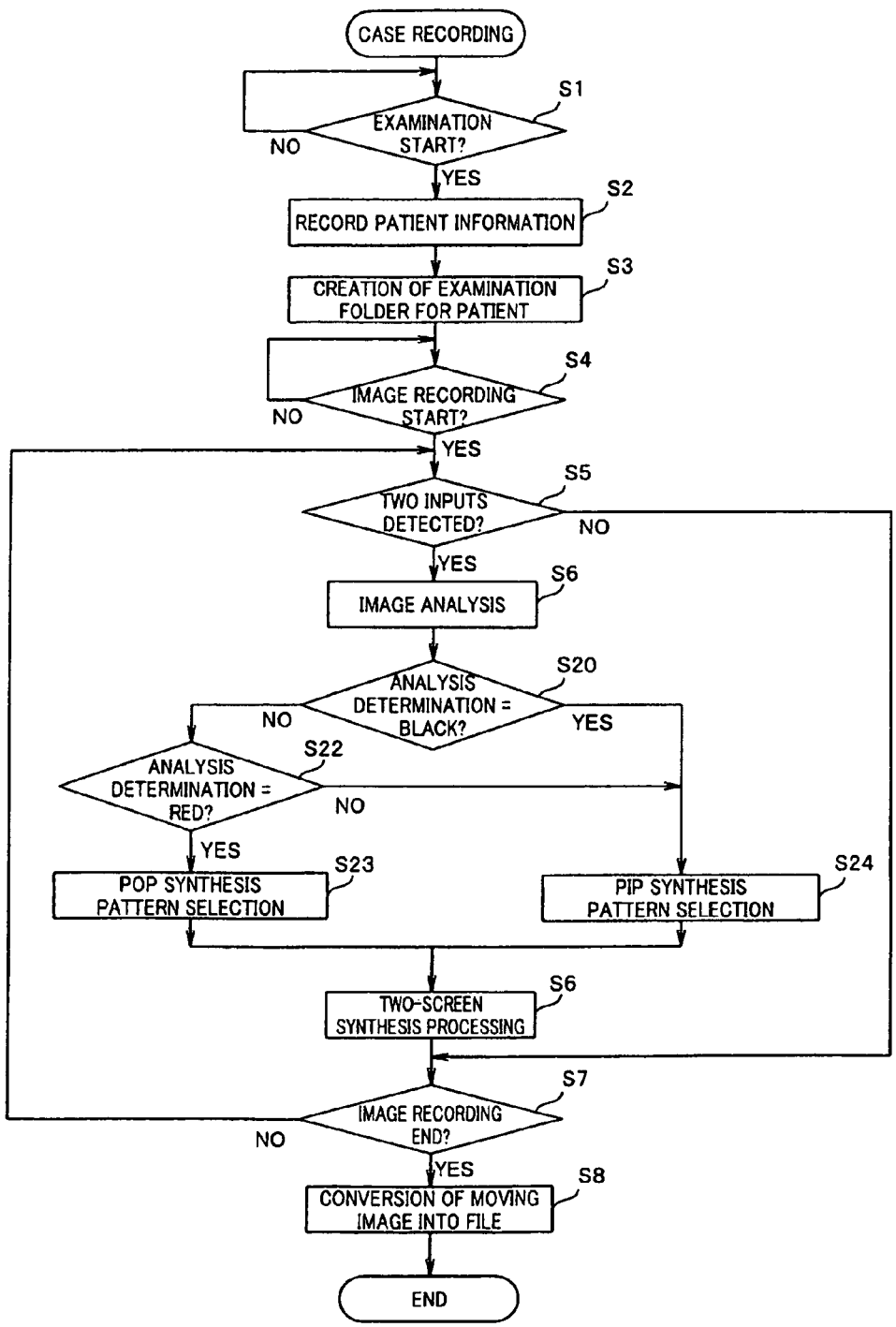
FIG. 6 is a flowchart illustrating an operation flow employed in a second embodiment of the present invention.

FIG. 6 is a flowchart illustrating an operation flow employed in a second embodiment of the present invention. In FIG. 6, procedures that are the same as in FIG. 5 are denoted by the same reference symbols and a description thereof is omitted hereunder. A hardware configuration of the present embodiment is similar to that of the first embodiment, and the present embodiment differs from the first embodiment only with respect to screen synthesis processing.

In the first embodiment an example was described in which two-screen synthesis processing is performed in accordance with a synthesis pattern that the control portion 28 sets. In the present embodiment, image analysis of a medical image is performed, and an optimal two-screen synthesis pattern is automatically selected based on the analysis result. As one example, in the case of an endoscope during an actual operation, images from the endoscope and an operative field camera are usually subjected to screen synthesis and recorded until a lesioned part is reached. By capturing images of the state of the surgeon's hands and the manner of treatment, the approach of the endoscope as far as the lesioned part can be precisely ascertained and such images serve as educational data. At this time, the most suitable screen synthesis is that performed according to the picture-in-picture technique in which the endoscopic image is disposed in a main screen since the endoscopic image is the most important image, and an operative field image that is not directly related to the medical treatment is disposed in a sub-screen. Next, after the endoscope arrived at the lesioned part, an endoscopic image from another endoscope processor is subjected to screen synthesis and recorded. This serves as educational data for identifying a resection range of a luminal organ by comparing two endoscopic images. At this time, since both of the endoscopic images are important, screen synthesis according to the picture-out-picture technique is the most suitable. Thus, it can be said that enabling recording according to the most suitable type of screen synthesis automatically without the surgeon changing the equipment settings during medical action contributes to improvement of medical knowledge and treatment accuracy, and enables more efficient medical treatment.

In the present embodiment, the operation flow up to the processing that detects two inputs in step S5 in FIG. 5 is the same as in the first embodiment. FIG. 6 illustrates processing with respect to a second input in a case where recording processing of a medical image Ima that is based on a video signal from the endoscope processor 10 as one input has started.

Figure 7:
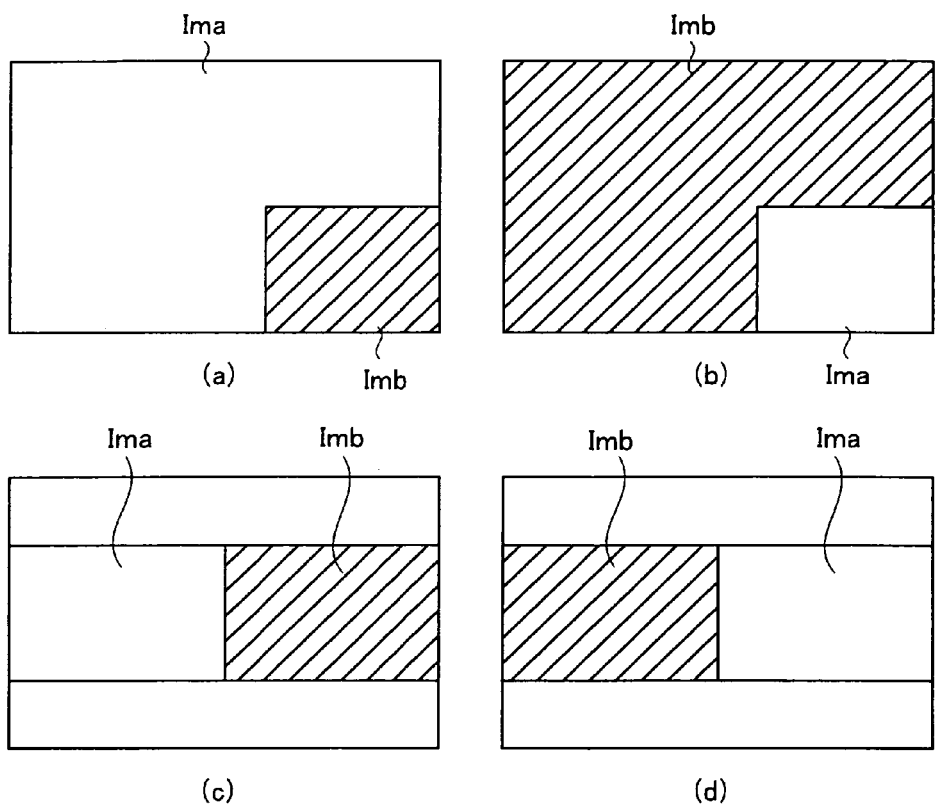
FIG. 7 is an explanatory view that illustrates examples of a synthesis pattern.

FIG. 7 is an explanatory view that illustrates examples of synthesis patterns. FIGS. 7(a) and (b) illustrate synthesis patterns in the picture-in-picture (PIP) format. FIG. 7(a) illustrates an example in which a medical image Ima that is based on a video signal inputted through the I/F 22 is taken as a main image, and a medical image Imb that is based on a video signal inputted through the I/F 23 is disposed as a sub-screen within the main image. FIG. 7(b) illustrates an example in which the medical image Imb is taken as the main image, and the medical image Ima is disposed as a sub-screen within the main image.

FIGS. 7(c) and (d) illustrate synthesis patterns in the picture-out-picture (POP) format. FIG. 7(c) illustrates an example in which a medical image Ima that is based on a video signal inputted through the I/F 22 is disposed on the left side of the screen, and a medical image Imb that is based on a video signal inputted through the I/F 23 is disposed on the right side of the screen. FIG. 7(d) illustrates an example in which the medical image Imb is disposed on the left side of the screen, and the medical image Ima is disposed on the right side of the screen. Note that in the synthesis patterns in FIGS. 7(c) and (d), a portion without an image is provided at the top and bottom of the screen so as not to change the aspect ratios of the medical images Ima and Imb.

In step S20 in FIG. 6, the screen synthesis calculation portion 29 performs image analysis of an inputted medical image. Based on the result of the image analysis, the screen synthesis calculation portion 29 determines whether or not the medical image is a dark image in step S20, and determines whether or not the medical image is a reddish color in step S22.

For example, in a case where a medical image is an endoscopic image, the inputted medical image is an overall reddish color due to the influence of the color of organs and blood or the like. In addition, for example, in a case where a medical image is an X-ray image or an ultrasound image, the inputted medical image is a black-and-white image. Further, in a case where a medical image is an image showing a scene in the operation room or the like, the overall color of the inputted medical image is a green or blue color.

Figure 8:
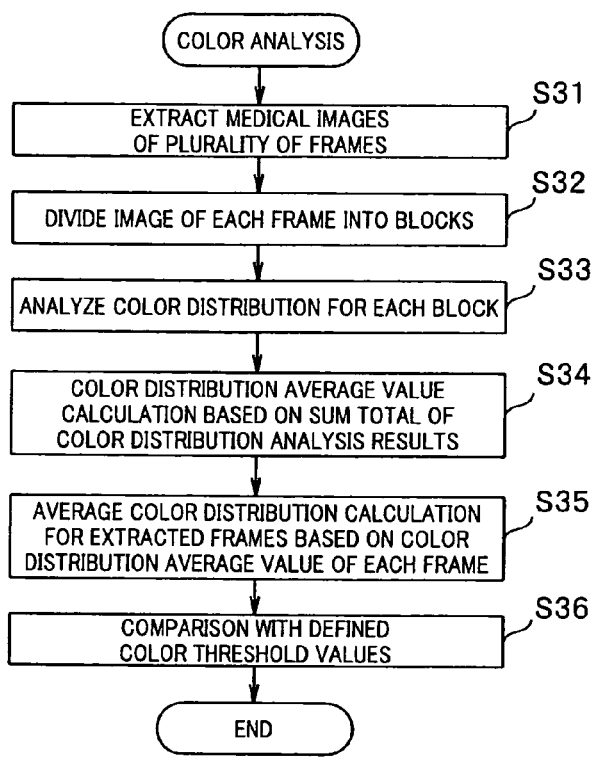
FIG. 8 is a flowchart illustrating an example of a color determination flow that determines a color of a medical image.
Figure 9:
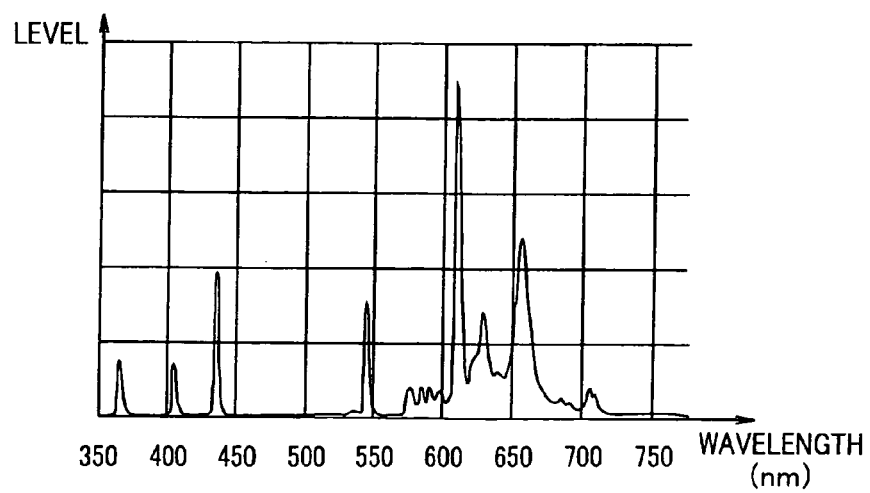
FIG. 9 is a graph illustrating a color distribution in respective blocks, in which the horizontal axis represents a wavelength and the vertical axis represents a level of each block.

FIG. 8 is a flowchart that illustrates an example of a color determination flow that determines a color of a medical image. FIG. 9 is a graph illustrating a color distribution in respective blocks, in which the horizontal axis represents a wavelength and the vertical axis represents a level of each block.

In step S31 in FIG. 8, the screen synthesis calculation portion 29 extracts medical images of a plurality of frames, and in step S32 divides the image of each frame into blocks. The screen synthesis calculation portion 29 analyzes the color distribution of each block. FIG. 9 illustrates an example of a color distribution in predetermined blocks of a predetermined medical image. The example in FIG. 9 illustrates that a level at a wavelength of 600 nm is comparatively high for the target block, and it is thus found that the target block is a reddish color.

In step S34, the screen synthesis calculation portion 29 determines the sum total of the single frame with respect to the analysis results for the color distribution of the respective blocks, and calculates a color distribution average value. In addition, in step S35, the screen synthesis calculation portion 29 calculates the average color distribution for the extracted frames based on the color distribution average value of the respective frames. The screen synthesis calculation portion 29 determines a color of the medical image by a comparison between the average color distribution and color threshold values that are defined in correspondence with the respective colors (step S36).

In a case where the result of analysis of the medical image in step S21 indicates that the medical image is a dark image, next, in step S24, the screen synthesis calculation portion 29 selects a synthesis pattern in the PIP format, and synthesizes the medical image that is inputted second as a sub-screen. If the medical image is not a dark image and the screen synthesis calculation portion 29 detected in step S22 that the medical image is not a reddish image either, in step S24 the screen synthesis calculation portion 29 selects a synthesis pattern in the PIP format, and synthesizes the medical image that is inputted second as a sub-screen. In contrast, in a case where the medical image is not a dark image and the screen synthesis calculation portion 29 detected in step S22 that the medical image is a reddish image, in step S23 the screen synthesis calculation portion 29 selects a synthesis pattern in the POP format, and disposes the medical image that is inputted second on the right side or left side of the screen and performs synthesis.

The remaining processing is the same as in the flow in FIG. 5.

Next, operations of the embodiment configured in this manner will be described.

It is assumed that an endoscopic image is inputted to the I/F 22 of the medical information recording apparatus 20 as a video signal that is inputted first. The endoscopic image is processed by the screen synthesis calculation portion 29, and the recording processing portion 30 starts recording processing of an original moving image that is based on the endoscopic image to the internal HDD 31 (step S4).

Here, it is assumed that a medical image that is inputted second is inputted to the I/F 23. The medical image is provided to the screen synthesis calculation portion 29, and the screen synthesis calculation portion 29 determines the color of the medical image that is inputted second by image analysis. In the case of the connections illustrated in FIG. 1, the second input is an ultrasound image, and therefore, in step S21, the screen synthesis calculation portion 29 determines that the image that is inputted second is a dark image, and shifts the process to step S24. In step S24, as shown in FIG. 7(a), the screen synthesis calculation portion 29 disposes the endoscopic image that is inputted first (medical image Ima) as a main image and disposes the ultrasound image that is inputted second (medical image Imb) as a sub-screen.

As an image for endoscopic diagnosis and the like, it is normally preferable that an endoscopic image is easier to observe than an ultrasound image. In the present embodiment, the kind of medical image is determined by determining the color of the medical image by image analysis, and screen synthesis that is suitable for the display or the like can be automatically performed by selecting a screen synthesis pattern in accordance with the determined result.

Note that in a case where the second input is a medical image that photographed the appearance of the operation room also, the process shifts from step S22 to step S24 and the second input is displayed as a sub-screen. Further, in a case where the second input is an endoscopic image from an unshown other endoscope processor, the process shifts from step S22 to step S23, and as shown in FIGS. 7(c) and (d), for example, screen synthesis is performed in accordance with the picture-out-picture technique in which the inputted two medical images are disposed on the left and right sides. Note that a configuration may also be adopted in which the synthesis pattern is forcedly changed between the patterns shown in FIGS. 7(a) to (d) by operating the input apparatus 11.

Thus, the same advantages as in the first embodiment are obtained according to the present embodiment, and screen synthesis that is suitable for the display can also be performed automatically by analyzing the colors of images.

(First Modification)

In the description of the second embodiment an example was described in which the color of a medical image is determined by image analysis, and a synthesis pattern is determined in accordance with the color determination result. However, a configuration may also be adopted in which contours that appear in a medical image are adopted as a criterion for determining a synthesis pattern. For example, it can be considered that compared to an image that photographed the appearance of an operation room, in an endoscopic image the picture is coarse and the image contains a small amount of contours. Therefore, an endoscopic image and other kinds of images can be distinguished by detecting contours in the images.

Figure 10:
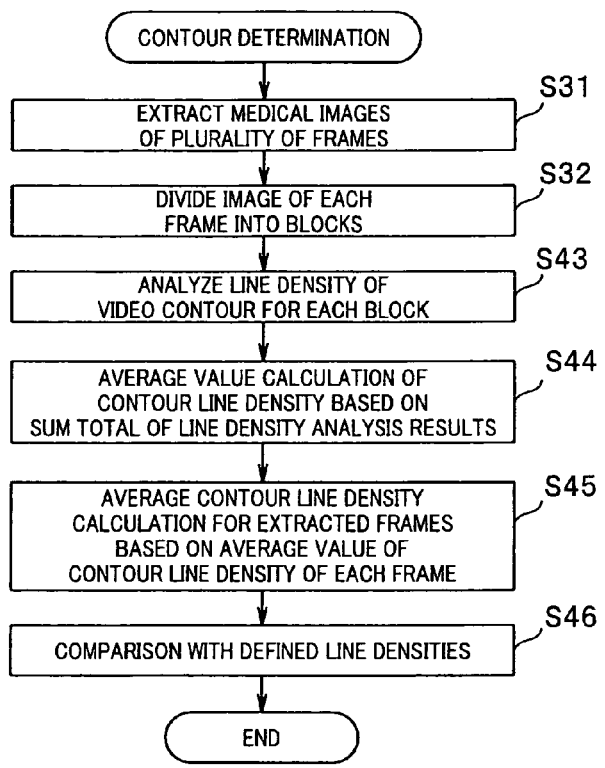
FIG. 10 is a flowchart illustrating an example of a contour determination flow that determines a contour of a medical image.
Figure 11:
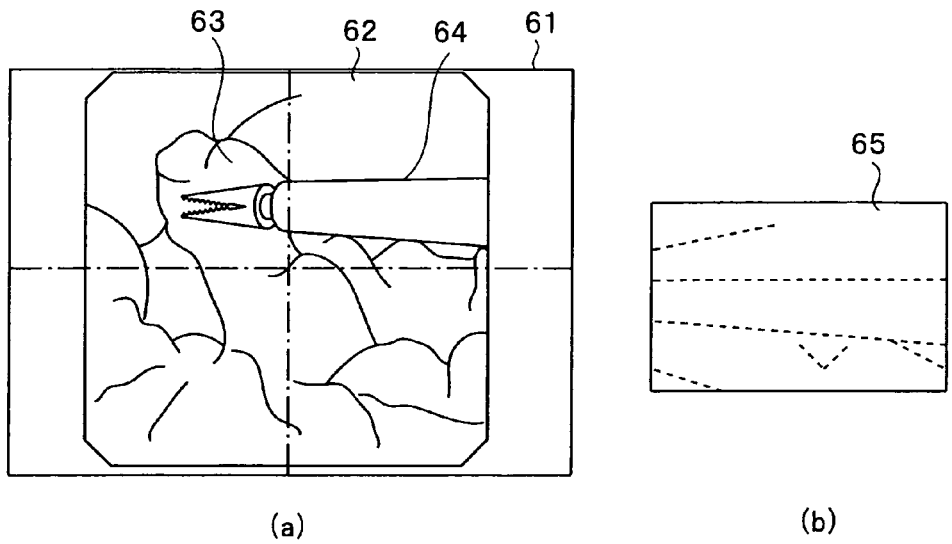
FIG. 11 is an explanatory view for describing contours in an endoscopic image.

FIG. 10 is a flowchart that illustrates an example of a contour determination flow that determines contours in a medical image. In FIG. 10, procedures that are the same as in FIG. 8 are denoted by the same reference symbols and a description thereof is omitted hereunder. FIG. 11 is an explanatory view for describing contours in an endoscopic image.

In step S43 in FIG. 10, the screen synthesis calculation portion 29 analyzes the line density of a video contour of each block. FIG. 11(a) illustrates an endoscopic image, and FIG. 11(b) illustrates a video contour. An endoscopic image 62 is disposed at the center of a screen 61. An internal organ 63 and a forceps 64 are shown in the endoscopic image 62. For example, the screen synthesis calculation portion 29 divides the endoscopic image 62 into four blocks at the boundaries indicated by the chain lines. In FIG. 11(b), video contours that the screen synthesis calculation portion 29 detected with respect to the right-upper block among the four blocks shown in FIG. 11(a) are illustrated with broken lines. As shown in FIG. 11(b), the line density of video contours of the blocks inside the endoscopic image 62 is comparatively low.

In step S44, the screen synthesis calculation portion 29 determines the sum total for one frame with respect to the results of analysis of the contour line density of each block, and calculates an average value of the contour line density. In addition, in step S45, the screen synthesis calculation portion 29 calculates the average contour line density for the extracted frames based on the average values of the contour line density of the respective frames. The screen synthesis calculation portion 29 determines the kind of the medical image by comparing the average contour line density and average contour line densities that are defined in correspondence with the respective images (step S46).

For example, if the average contour line density is equal to or less than a predetermined threshold value, the screen synthesis calculation portion 29 determines that the target medical image is an endoscopic image, while if the average contour line density exceeds the threshold value the screen synthesis calculation portion 29 determines that the target medical image is an image other than an endoscopic image, for example, an image that photographed the appearance of the operation room.

Similarly to FIG. 6, the screen synthesis calculation portion 29 selects a synthesis pattern in the PIP or POP format based on the determination result with respect to the video contours, and performs screen synthesis.

In addition, as another modification, a configuration may be adopted in which a determination as to whether a medical image that is inputted second is an endoscopic image or an image other than an endoscopic image is made by performing an image comparison between an endoscopic image that is inputted first and a medical image that is inputted second.

(Second Modification)

Figure 12:
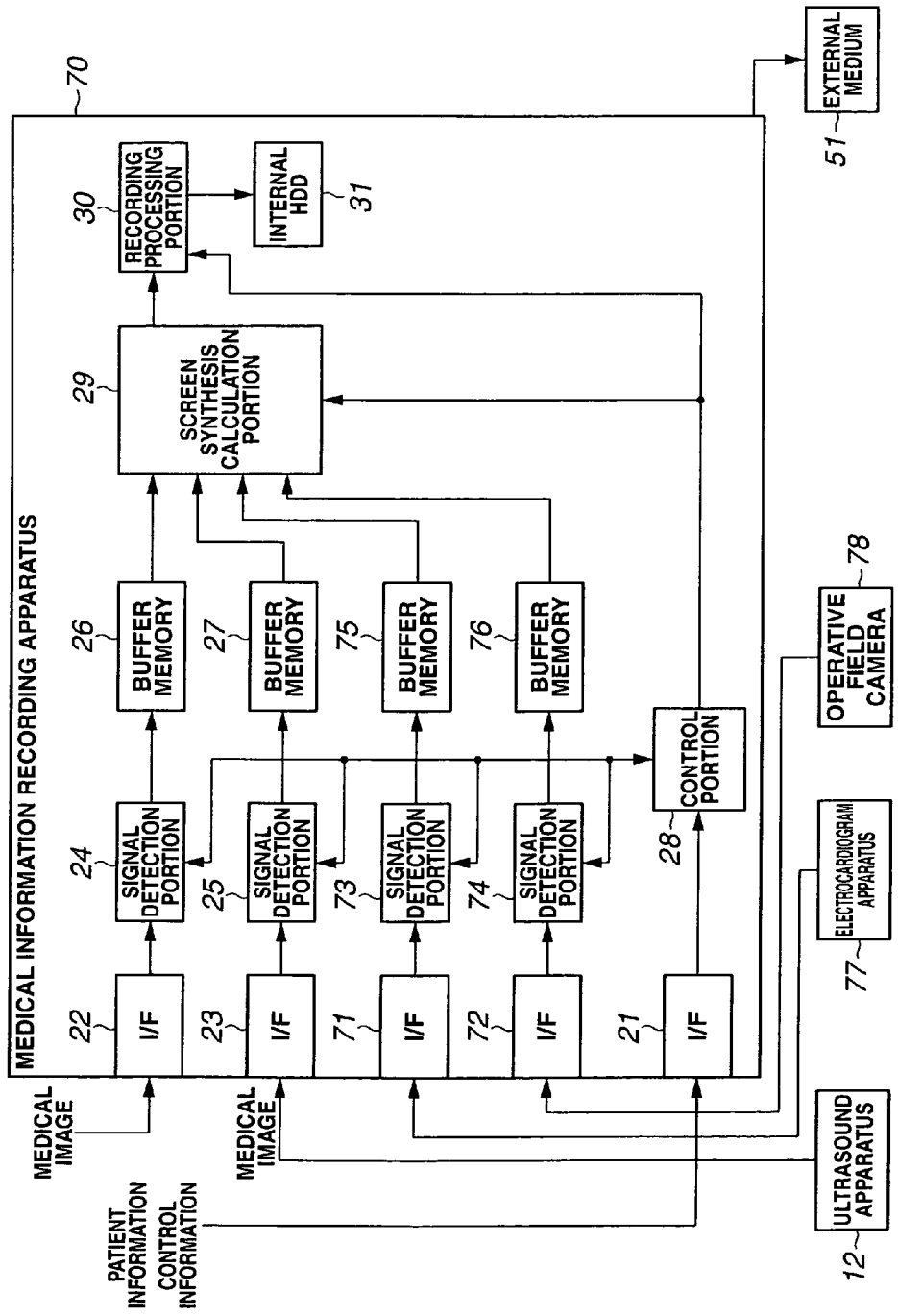
FIG. 12 is a block diagram illustrating the configuration of a second modification.
Figure 13:
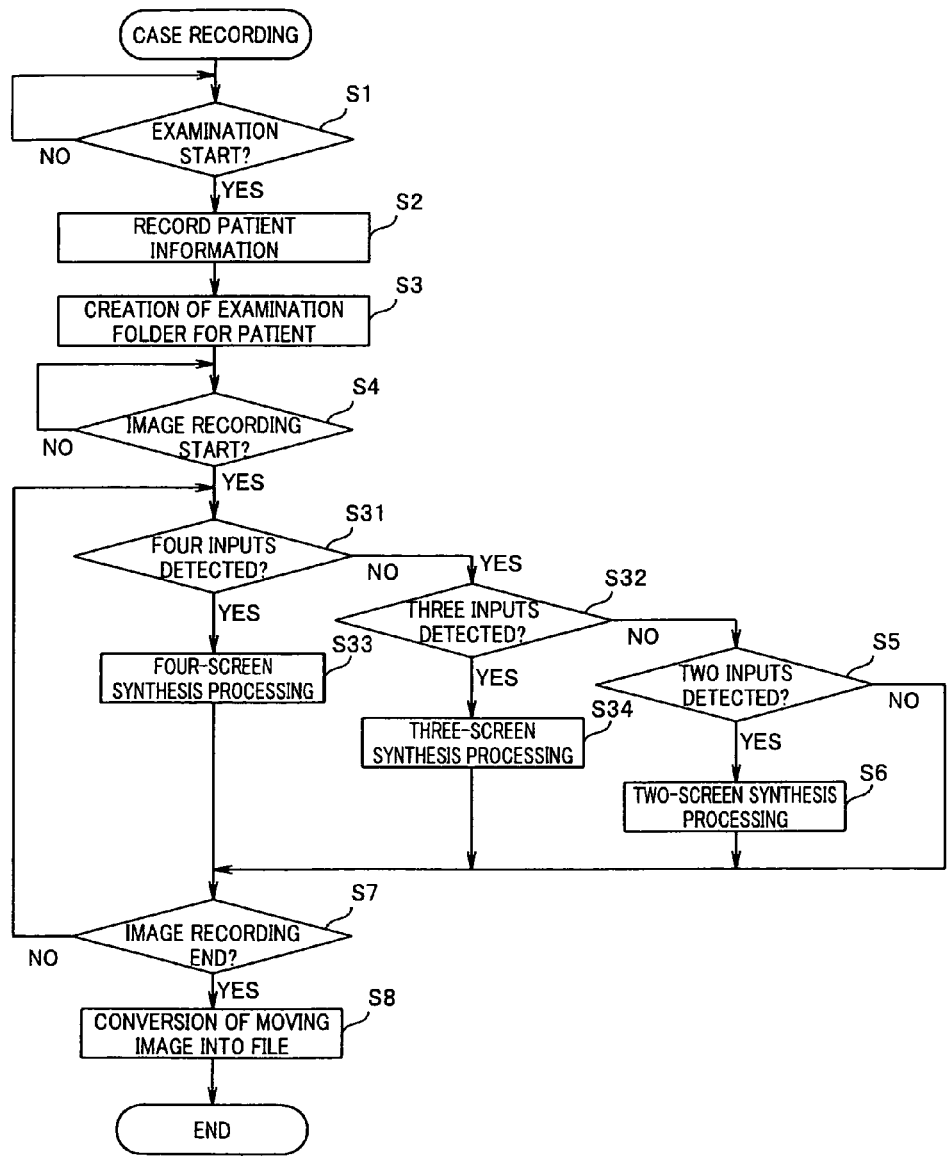
FIG. 13 is a flowchart for describing operations of the second modification.

FIG. 12 to FIG. 14 illustrate a second modification that illustrates an example in which there are three or more inputs. FIG. 12 is a block diagram that illustrates the configuration of the second modification. FIG. 13 is a flowchart for describing operations of the second modification. FIG. 14 is an explanatory view for describing synthesis patterns of the second modification. Components in FIG. 12 that are the same as in FIG. 1 are denoted by the same reference numbers and a description thereof is omitted hereunder. Further, procedures in FIG. 13 that are the same as in FIG. 5 are denoted by the same reference symbols and a description thereof is omitted hereunder.

The second modification differs from the configuration illustrated in FIG. 1 only in the respect that there are four input systems according to the second modification. Note that diagrammatic representation of the input apparatus 11, the endoscope processor 10, and the monitor 40 is omitted from FIG. 12 to simplify the drawing.

In the configuration shown in FIG. 12, in addition to the endoscope processor 10 (see FIG. 1) and the ultrasound apparatus 12, an electrocardiogram apparatus 77 and an operative field camera 78 are adopted as apparatuses that output a medical image. A medical image from the electrocardiogram apparatus 77 is taken in to a medical information recording apparatus 70 through an I/F 71, and a medical image from the operative field camera 78 is taken in to the medical information recording apparatus 70 through an I/F 72.

A video signal inputted through the I/F 71 is supplied to a buffer memory 75 via a signal detection portion 73. A video signal inputted through the I/F 72 is supplied to a buffer memory 76 via a signal detection portion 74. The configurations of the I/F 71 and I/F 72 is the same as the configuration of the I/F 22 and I/F 23. The configuration of the signal detection portions 73 and 74 is the same as the configuration of the signal detection portions 24 and 25. The configuration of the buffer memories 75 and 76 is the same as the configuration of the buffer memories 26 and 27. Video signals inputted through the I/Fs 22, 23, 71, and 72 are temporarily stored in the buffer memories 26, 27, 75, and 76, respectively, and thereafter are provided to the screen synthesis calculation portion 29.

The control portion 28 controls the signal detection portions 24, 25, 73, and 74 to acquire detection results regarding whether or not video signals were inputted through the I/Fs 22, 23, 71, and 72, and outputs a synthesis control signal that is based on the detection results to the screen synthesis calculation portion 29. The screen synthesis calculation portion 29 performs synthesis processing with respect to the inputted medical images based on the synthesis control signal.

The flow illustrated in FIG. 13 differs from the flow illustrated in FIG. 5 only in the respect that the processing of steps S31 to S34 is added to the flow in FIG. 13. In steps S31, S32, and S5, it is determined whether or not there are four inputs, whether or not there are three inputs, and whether or not there are two inputs, respectively. If there are four inputs, four-screen synthesis processing is performed in step S33. If there are three inputs, three-screen synthesis processing is performed in step S34. If there are two inputs, two-screen synthesis processing is performed in step S6.

FIG. 14 illustrates an example of synthesis patterns, in which FIG. 14(a) is an example of three-screen synthesis and FIG. 14(b) is an example of four-screen synthesis. The example illustrated in FIG. 14 are both examples in the POP format. FIG. 14(a) illustrates an example in which a medical image Ima that is based on a video signal inputted through the I/F 22 is disposed in a large portion on the left side of the screen, and medical images Imb and Imc that are based on video signals inputted through the I/Fs 23 and 71 are disposed at the top and bottom on the right side of the screen. FIG. 14(b) illustrates an example in which medical images Ima to Imd that are inputted through the I/Fs 22, 23, 71, and 72, respectively, are disposed in regions obtained by dividing the screen into four parts that are at the top left, top right, bottom left, and bottom right thereof.

Thus, according to the second modification, inputting or the stopping of the inputting of medical images of four inputs is detected, screen synthesis processing of the medical images of the four inputs is controlled based on the detection results, and an original moving image that is in accordance with changes in the inputs that occur even during recording can be recorded as a single moving image file. Note that although an example in which there are four inputs is described according to the second modification, it is clear that it is possible to set the number of input systems as appropriate.

Next, a mechanism by which a two-screen synthesis format is selected and the contents of recorded data will be described together with the actual flow of procedures.

In a common surgical endoscope procedure, recording is started after a rigid endoscope is inserted into a cavity (step S4 in FIG. 6) [scene 1: time of ablation treatment towards lesioned part]. The procedure proceeds by advancing the endoscope towards a lesion site while treating adhered membranes or fat around the organ. At this time, since the treatment is not a comparatively advanced treatment, from the viewpoint of leaving a record verifying that appropriate treatment was performed, only the endoscopic image is recorded (loop of a "No" determination in step S5 and a "No" determination in step S7 in FIG. 6).

Upon reaching the lesion site, advanced treatment such as careful ablation or resection between the lesion site and neighboring organs is started. At this time, in order to leave a record of an image showing the state of the surgeon's hands that is synchronized with the endoscopic image with the intention of not only verifying that appropriate treatment was performed but also of using the record for education of young doctors, a video cable from an operative field camera is connected to the medical information recording apparatus [scene 2: time of treatment after reaching lesioned part]. As a result, an input terminal is automatically set based on the video signal that is detected by the medical information recording apparatus (FIG. 2). After the input terminal has been set, a video signal is inputted from the operative field camera to the screen synthesis calculation portion 29 through the signal detection portion 25 and the buffer memory 27 shown in FIG. 1, and cooperative control is performed from the control portion 28 to the screen synthesis calculation portion (step S5 in FIG. 6). At the screen synthesis calculation portion 29, image analysis starts automatically based on the inputted video signal (step S6 in FIG. 6). A PIP synthesis pattern is automatically set based on the color analysis of the video signal photographed by the operative field camera and the combined results of the determinations in step S21 and step S22 in FIG. 6, and recording of the moving image is continued while two-screen synthesis begins. Since it is intended to use the recorded image for educational use, the two-screen synthesis pattern shown in FIG. 7(a) in which the endoscopic image that is the most important image appears in the main screen and the operative field image appears in the sub-screen is selected at this time.

After treatment has proceeded to a certain degree, a flexible endoscope is used to identify the lesion site. At this time, in order to leave a record that clearly demonstrates the process up to lesion site identification and resection line determination with the intention of not only verifying that appropriate treatment was performed but also of using the record for education of young doctors, a video cable that transmits an endoscopic image that is outputted from another processor to which the flexible endoscope has been connected is connected to the medical information recording apparatus. At the same time, since treatment to identify the lesion site is stopped, the surgeon detaches the cable for the video input from the operative field camera [scene 3: time of identification of lesioned part]. Although in this case the cable is intentionally detached, in a case where the cable is not detached a configuration may be adopted that includes means that automatically switches to the second video input terminal upon detection of the second input signal by the signal detection portion 25. As a result, an input terminal is automatically set again based on the video signal that is detected by the medical information recording apparatus (FIG. 2). Similarly to the foregoing description, after the input terminal has been set, a video signal is inputted to the screen synthesis calculation portion 29 through the signal detection portion 25 and the buffer memory 27 shown in FIG. 1 from the other processor to which the flexible endoscope is connected, and cooperative control is performed from the control portion 28 to the screen synthesis calculation portion (step S5 in FIG. 6). At the screen synthesis calculation portion 29, image analysis starts automatically based on the inputted video signal (step S6 in FIG. 6). A POP synthesis pattern is automatically set based on the color analysis of the video signal observed with the flexible endoscope and the combined results of the determinations in step S21 and step S22 in FIG. 6, and recording of the moving image continues while two-screen synthesis begins. Since it is intended to use the recorded image for educational use, because an endoscopic image from the rigid endoscope and an endoscopic image from the flexible endoscope are of equal medical importance, the two-screen synthesis pattern shown in FIG. 7(c) in which the endoscopic image from the rigid endoscope is shown on the left side of the screen and the endoscopic image from the flexible endoscope is shown on the right side of the screen is selected at this time.

When a resection line for an organ is determined, resection is started with a view to removing the lesion site. The treatment at this time is an advanced treatment similarly to the treatment described above. Therefore, in order to leave a record of an image showing the state of the surgeon's hands that is synchronized with the image obtained by the rigid endoscope with the intention of not only verifying that appropriate treatment was performed but also of using the record for education of young doctors, the video cable from the operative field camera is reconnected to the medical information recording apparatus [scene 4: time of resection and anastomosis after lesioned part identification]. Similarly to the above description, the medical information recording apparatus that took in the video signal from the operative field camera sets an input terminal automatically, and performs color analysis based on the inputted video signal. Based on the analysis result, a PIP pattern for two-screen synthesis (FIG. 7(a)) in which the endoscopic image appears in the main screen and the operative field image appears in the sub-screen is selected again, and recording of the moving image is continued while performing two-screen synthesis.

Since a high level of technical skill is required to perform anastomosis by a forceps operation when performing anastomosis of the resected part and checking for bleeding after removal of the lesion site also, recording of a moving image according to two-screen synthesis of the endoscopic image and the operative field image is continued.

After anastomosis, the in-vivo part is cleaned. Since the treatment at this time is a simple treatment and not a high-level medical action and there is no longer an educational purpose to record the treatment, the video cable from the operative field camera is detached, and recording of a moving image of only the endoscopic image continues [scene 5: time of treatment after removal of lesioned part].

Finally, the wound is closed. At this time, since the rigid endoscope itself is removed to outside the body, the video cable from the processor to which the endoscope was connected is detached. In place thereof, the video cable from the operative field camera is reconnected to the medical information recording apparatus, and recording of a moving image of only the operative field image continues [scene 6: time of wound closure].

The recording is stopped when the procedure ends. Thereupon, a single moving image file is generated in which images are incorporated that were subjected to two-screen synthesis during the series of procedures.

Thus, the control portion 28 and the screen synthesis calculation portion 29 can determine a scene or determine switching of a scene according to a connection state or input state of an input terminal, an image analysis result for a video signal, and the like, and can select a screen synthesis format that is most suitable for each scene and also decide the data that is to be recorded.

Note that in the above description an example has been described that follows a common surgical endoscope procedure, and in which, as an example in which steps of the procedure are previously determined, respective scenes are determined and a screen synthesis format is selected in accordance with only a determination as to whether or not devices are connected to input terminals and the results of image analysis. In addition, in the case of fixing the devices that are connected to the respective input terminals, it is also possible to presume the respective scenes based on determination results regarding whether or not devices are connected to the respective input terminals. Thus, for example, in a case where the relevant devices are connected to an input terminal for a rigid endoscope and an input terminal for an operative field camera, screen synthesis can be performed that employs an image from the rigid endoscope as a main screen and employs an image from the operative field camera as a sub-screen.

(Third Embodiment)

Figure 15:
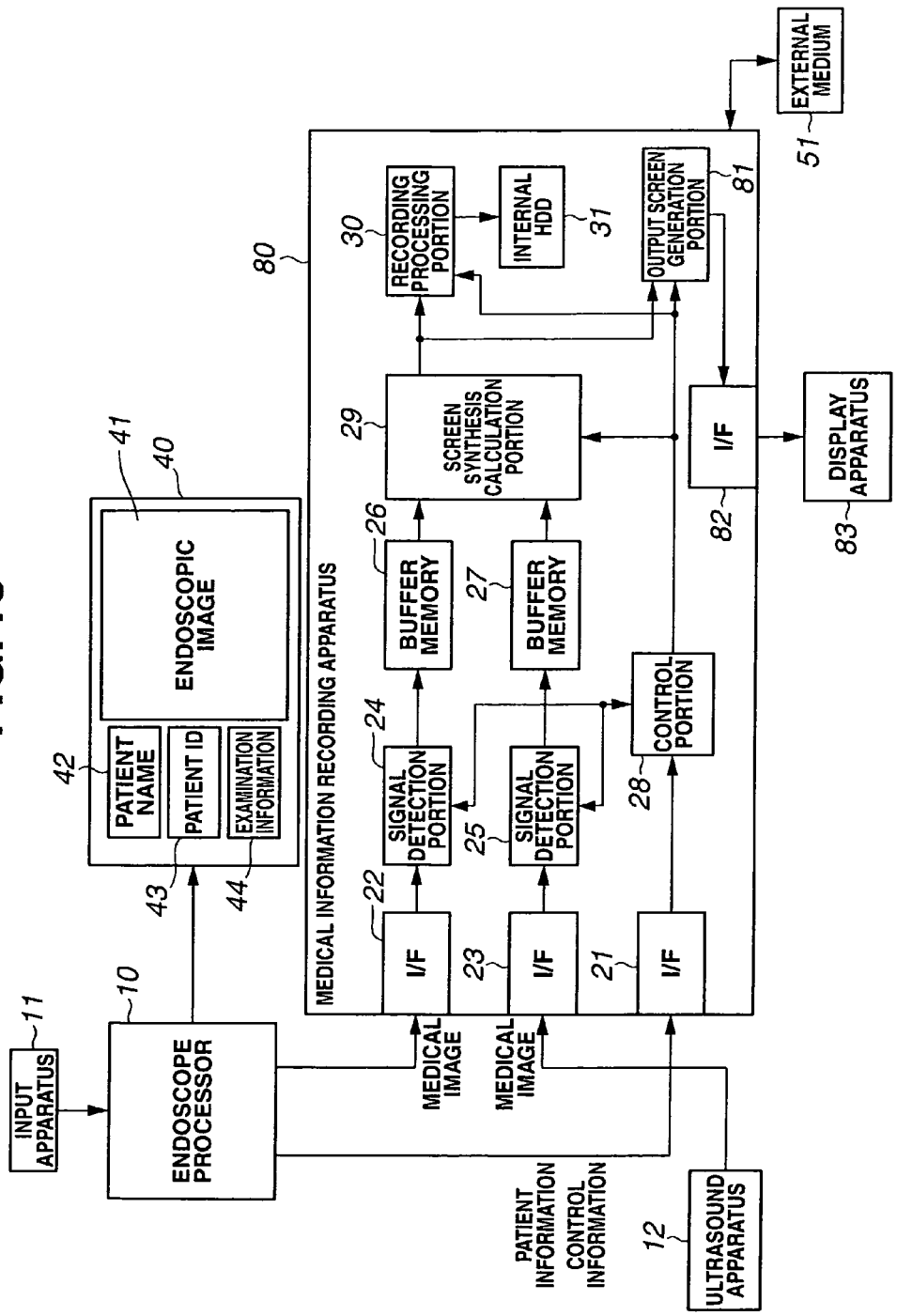
FIG. 15 is a block diagram illustrating a third embodiment of the present invention.

FIG. 15 is a block diagram that illustrates a third embodiment of the present invention. Components in FIG. 15 that are the same as in FIG. 1 are denoted by the same reference numbers and a description thereof is omitted hereunder.

Many conventional recording apparatuses include a display that shows the operating state of the recording apparatus and operation buttons which are disposed on a front face portion of the recording apparatus casing. However, depending on the operation room in which the recording apparatus is installed or the placement thereof on a trolley system that can transport medical equipment, in some cases the visibility of the front face portion of the recording apparatus casing is poor and the operating status is difficult to check, or the operability is extremely poor. In such cases in which it is difficult to ascertain the status of the recording apparatus, there is a risk that a situation may arise which hinders smooth progress of the medical action or in which a record verifying that appropriate medical action is performed cannot be made, such as starting recording without noticing that the recording capacity is insufficient or failing to ascertain an abnormal state of a device during recording.

Therefore, according to the present embodiment a configuration is adopted in which various kinds of information can be displayed on a display apparatus that is an external monitor, and not just on a display portion disposed on a front face portion of the recording apparatus casing. A medical information recording apparatus 80 of the present embodiment differs from the medical information recording apparatus 20 of the first embodiment in that the medical information recording apparatus 80 includes an output screen generation portion 81 and an I/F 82.

The output screen generation portion 81 is configured to be capable of providing an image that is the same as an image that is displayed on a display portion disposed on a front face portion of an unshown recording apparatus casing to a display apparatus 83 constituted by a liquid crystal monitor or the like through the I/F 82 to display the image thereon. During recording of a medical image, the output screen generation portion 81 generates not only a medical image (synthesized image) from the screen synthesis calculation portion 29, but also generates an output screen for image display that is based on various kinds of information relating to the recording state such as, for example, an image quality setting at the time of recording, the number of titles at the time of recording, the number of chapters, and the remaining recording capacity of the internal HDD 31.

Note that although only one I/F 82 is shown in FIG. 15, a plurality of interfaces for video output can be adopted. For example, video interfaces for SDI and DVI and the like can be adopted and images can be outputted to display apparatuses corresponding to these interfaces. Further, by utilizing Ethernet (registered trademark) as an interface, a video can be outputted using the HTTP protocol or streaming, and it is also possible to output images to a display portion of an external computer.

The output screen generation portion 81 outputs an output screen for display after converting the output screen to a format that is suited to the interface of the display apparatus 83. In a case where there are a plurality of interfaces and not just the I/F 82, it is possible to output the output screen for display from an interface that is specified from among the plurality of interfaces, and it is also possible to adopt a configuration that outputs an output screen for display from all the interfaces.

In the present embodiment, the output screen generation portion 81 can generate an output screen in a first and a second display mode.

The first display mode is a mode that displays an image that is inputted to the recording processing portion 30 without changing the image size thereof. In this display mode, the image that is a recording target can be displayed in high resolution.

The second display mode is a mode that displays information relating to the recording state of the main apparatus. In the second display mode, the recording state of the display apparatus 83 can be checked without looking at the display portion disposed on the front face of the recording apparatus casing.

FIG. 16 is an explanatory view that illustrates a display example of the second display mode. FIG. 16(a) illustrates a display example in a case where there is a single original moving image as a recording target. FIG. 16(b) illustrates a display example in a case where two original moving images exist simultaneously as recording targets. Note that the synthesized image in the respective embodiments described above is a single original moving image.

As shown in FIG. 16(a), the second display mode has a plurality of display regions 202 to 211 in a display screen 201. The display region 202 is a region that displays patient information, for example, a patient ID or a patient name, that is inputted from the endoscope processor 10 (see FIG. 1) and the like. Information showing whether the patient is currently being examined or is not being examined is also displayed in the display region 202. Although in the example shown in FIG. 16(a) it is shown that the patient is being examined by displaying the information "under examination", in a case where the patient is not being examined the information "not under examination" or the like is displayed. Further, although an example is illustrated in FIG. 16(a) in which information is displayed using text (a character string), information can also be displayed using icons or the like.

In a display region 203, information is displayed that shows the recording settings, such as the input terminal to which a medical image that is the recording target is inputted, whether the image is a moving image or a still image, and the like. In the example shown in FIG. 16(a), information displayed in the display region 203 shows that a video signal in SDI format is inputted, and that recording in "high image quality" mode is specified for a moving image, and recording in "high compression" mode in "JPEG" format is specified for a still image.

In a display region 204, the medical image that is the recording target is displayed in a reduced image size. Further, the current recording duration is displayed at the bottom left of the display region 204, and the image recording state, such as whether image recording is in progress, is stopped, or is temporarily stopped, is displayed by means of an icon or text or the like at the bottom right of the display region 204. In the example illustrated in FIG. 16(a), "⊙ REC" is used to show that image recording is currently in progress.

A display region 205 displays the number of still images recorded during the current examination. Images that have been recorded during the current examination are displayed as thumbnail images in three display regions 206 below the display region 205. In the example illustrated in FIG. 16(a), a configuration is adopted so as to display thumbnail images of the past three images in the display regions 206, and to update an old image to a new image when the new image is recorded. Note that although the number of images that are displayed in the example illustrated in FIG. 16(a) is three, a configuration can also be adopted that enables the display of a larger number of images. The surgeon can confirm that still images are definitely being acquired by referring to the display regions 206.

The number of titles of moving images that have been recorded during the current examination is displayed in the display region 207. By performing operations to record and to stop the recording, titles are delimited from each other, a subfolder is generated for each title inside the patient folder, and a single original moving image is recorded. Moving image titles (original moving images) recorded during the current examination are displayed in the thumbnail format in three display regions 208 below the display region 207. Although in the example illustrated in FIG. 16(a) a configuration is adopted so as to display the past three titles, a configuration can also be adopted that enables the display of thumbnail images of a larger number of titles.

Information showing whether audio recording is enabled or disabled is displayed in the display region 209. The medical information recording apparatus 80 is capable of recording audio signals inputted from an unshown audio input terminal in conjunction with recording of a moving image. FIG. 16(a) illustrates an example in which the text "AUDIO ON" is displayed to indicate that audio recording is enabled. It is possible to switch between enabling/disabling audio recording in accordance with the settings. When audio recording is disabled, for example, text such as "AUDIO OFF" is displayed.

The remaining recording capacity of the internal HDD 31 is displayed in the display region 210. A recording time period for a moving image and a number of still images that can be recorded are displayed in the display region 210, and the values are updated in real time according to the state of the recording capacity. The medical information recording apparatus 80 can also be configured to display a warning when the remaining capacity becomes small, for example, when the remaining capacity falls below a certain threshold value.

The remaining recording capacity of the external medium 51 is displayed in the display region 211. In the example illustrated in FIG. 16(a), the type of medium that is the storage destination, a recording time period for a moving image, and a number of still images that can be recorded are displayed. The remaining recording capacity is updated in real time. Similarly to the configuration for the internal HDD 31, the medical information recording apparatus 80 can also be configured to display a warning when the remaining capacity of the external medium 51 becomes small, for example, when the remaining capacity falls below a certain threshold value.

FIG. 16(b) illustrates an example in a case where a plurality of images, for example, two images, that are the target of recording are displayed on the display screen 201, in which a display region relating to one of the images ("CH1") is indicated by a blank space, and a display region relating to the other of the images ("CH2") is indicated by a shaded part. Note that display regions in FIG. 16(b) that are the same as in FIG. 16(a) are denoted by the same reference numbers, and a description thereof is omitted hereunder.

In FIG. 16(b), the display regions 203a and 203b relate to CH1 and CH2, respectively, and are regions that display similar information as the display region 203 in FIG. 16(a). The display regions 204a and 204b relate to CH1 and CH2, respectively, and are regions that display medical images in a similar manner to the display region 204 in FIG. 16(a). In the example illustrated in FIG. 16(b), the display shows that image recording is in progress with respect to the medical image of CH1, and that image recording with respect to the medical image of CH2 is in a stopped state.

A display region 213 is a region that displays similar contents as the display region 205 in FIG. 16(a) for both CH1 and CH2. A display region 214 is a region that displays similar contents as the display region 207 in FIG. 16(a) for both CH1 and CH2. In these regions 213 and 214, information relating to CH1 is displayed after the text "CH1", and information relating to CH2 is displayed after the text "CH2".

Further, both a still image of CH1 and a still image of CH2 are displayed in the display regions 206 that display thumbnail images of still images. In the display regions 206, the text "CH1" or "CH2" is displayed below the thumbnail display so that the surgeon can know whether the relevant image is an image for CH1 or CH2. Likewise, the display regions 208 that display thumbnail images of moving images display both a moving image of CH1 and a moving image of CH2. In the display regions 208, the text "CH1" or "CH2" is displayed below the thumbnail display so that the surgeon can know whether the relevant image is an image for CH1 or CH2.

The surgeon can operate the input apparatus 11 to specify whether to select the first display mode or the second display mode. An operation signal relating to the display mode from the input apparatus 11 is supplied to the control portion 28 through the I/F 21. Based on the operation signal, the control portion 28 outputs a display control signal for specifying the display mode to the output screen generation portion 81. The output screen generation portion 81 generates an output screen of the first or second display mode in accordance with the display control signal from the control portion 28. Note that an operation to select the display mode is not limited to the input apparatus 11, and a configuration can also be adopted so as to perform an operation to select a display mode by means of an unshown button or touch panel on the apparatus body, an infrared remote control, or other external controller or the like.

In a case where the configuration includes only the I/F 82 as an interface, the display mode may be set by the control portion 28 or the display mode may be set in accordance with an operation performed by the surgeon. In a case where a plurality of interfaces are provided, a configuration may also be adopted so as to enable the surgeon or the like to individually specify which display mode to set in correspondence with the respective interfaces.

In this connection, in the display mode illustrated in FIG. 16(*b*), medical images of two inputs can be displayed without synthesizing the medical images. To enable such kind of display, the control portion 28 is configured so as to control the screen synthesis calculation portion 29 so that a setting can be made regarding whether to always enable screen synthesis or disable screen synthesis.

When a setting is made to always enable screen synthesis, when two video signals are inputted, simultaneously therewith the screen synthesis calculation portion 29 automatically starts synthesis processing, and a single moving image is obtained. In this case, the display in the display mode illustrated in FIG. 16(*a*) appears on the display screen of the display apparatus 83.

When a setting is made to disable screen synthesis, since synthesis processing is not performed even if two video signals are inputted, two moving images that correspond to the respective inputs are obtained. In this case, the display in the display mode illustrated in FIG. 16(*b*) appears on the display screen of the display apparatus 83.

Note that when a setting is made to disable screen synthesis, in a case where only one video signal is inputted, because screen synthesis processing is not performed at the screen synthesis calculation portion 29, the inputted medical image is displayed as a moving image in one region of the display regions 204*a* and 204*b* illustrated in FIG. 16(*b*), and no image (a black screen) is displayed in the other region. Note that when screen synthesis is disabled, two video signals (moving images) are transmitted between the screen synthesis calculation portion 29 and the recording processing portion 30, respectively (diagrammatic representation is omitted from the drawings).

(Fourth Embodiment)

Figure 17:
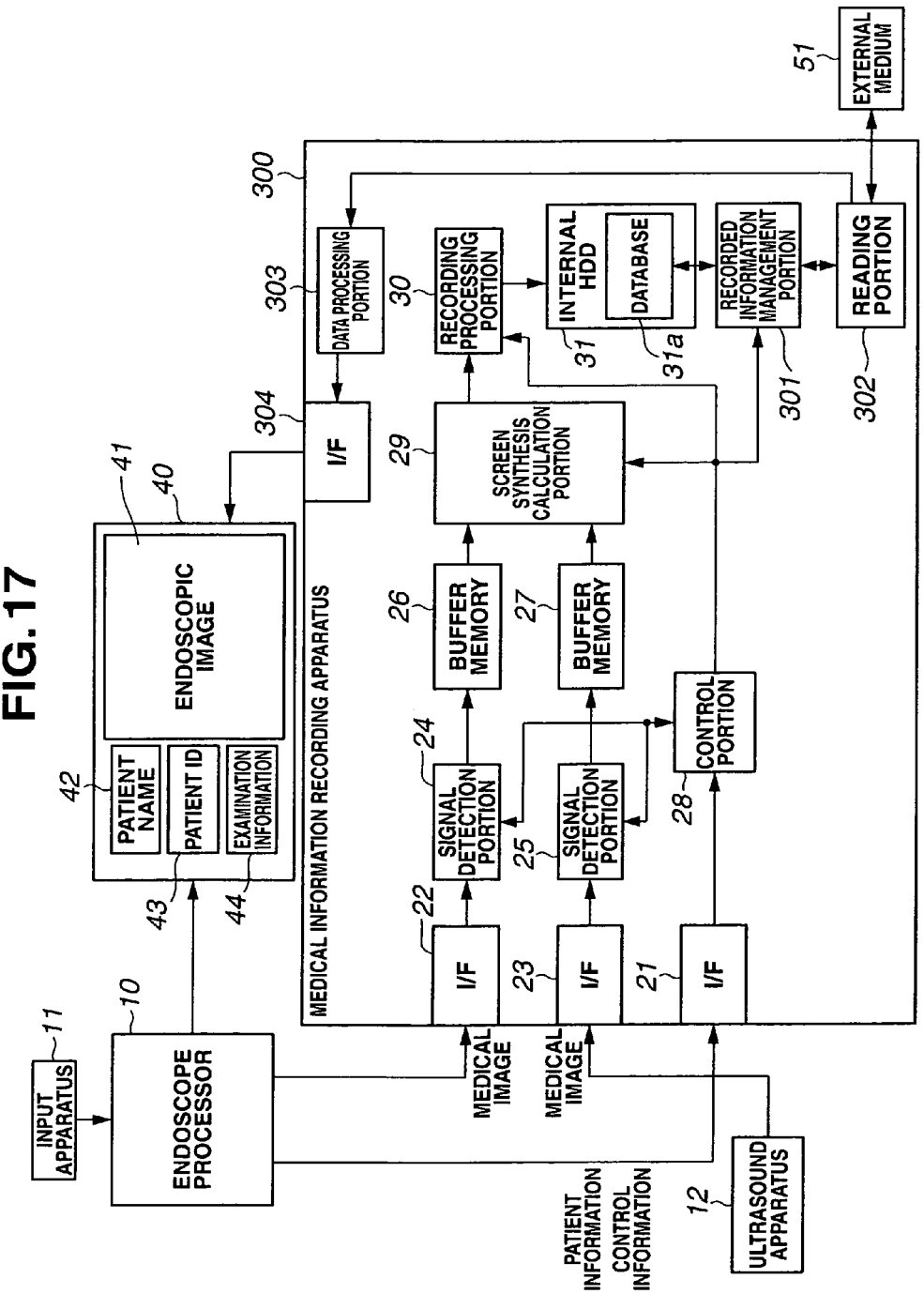
FIG. 17 is a block diagram illustrating a fourth embodiment of the present invention.

FIG. 17 to FIG. 20 relate to a fourth embodiment of the present invention. FIG. 17 is a block diagram illustrating the fourth embodiment. Components in FIG. 17 that are the same as in FIG. 1 are denoted by the same reference numbers and a description thereof is omitted hereunder.

Conventionally, in consideration of the fact that recorded data is utilized on a computer and the like, there are many cases where a recording apparatus for medical use is configured to also enable replication onto an external medium of recorded data that is recorded on the internal HDD. However, for reasons such as preventing the entry of viruses that may be present on an external medium, the recording apparatuses are set so that the recording apparatuses cannot read recorded data from an external medium on which recording has been completed. Consequently, once an external medium has been removed from the recording apparatus, it is not possible to thereafter utilize the recording apparatus to readily confirm the contents of the recorded data that was recorded on the external medium.

Therefore, the present embodiment is configured to enhance convenience while ensuring security by enabling reading of recorded data from an external medium on which recording has been completed, after performing a check with respect to the external medium and a recorded file.

A medical information recording apparatus 300 according to the present embodiment differs from the medical information recording apparatus 20 illustrated in FIG. 1 in that the medical information recording apparatus 300 additionally includes a recorded information management portion 301, a reading portion 302, a data processing portion 303, and an I/F 304. The reading portion 302 is controlled by the recorded information management portion 301, and is configured to be capable of reading data that is recorded on the external medium 51. The recorded data is provided to the data processing portion 303 from the reading portion 302, and the data processing portion 303 performs data processing to expand the data into a video signal, and outputs the resulting signal to the I/F 304. The I/F 304 is configured to provide the video signal from the data processing portion 303 to the monitor 40 to cause an image to be displayed.

In the present embodiment, the recorded information management portion 301 is controlled by the control portion 28 and is configured to perform a check with respect to an external medium on which recording was performed by the medical information recording apparatus 300, and to permit reading of recorded data from the external medium when it is determined as a result of the check that the external medium is an external medium on which written data was recorded. In order to perform the aforementioned check, the recorded information management portion 301 is configured to generate a database 31*a* and record the database 31*a* on the internal HDD 31.

Figure 18:
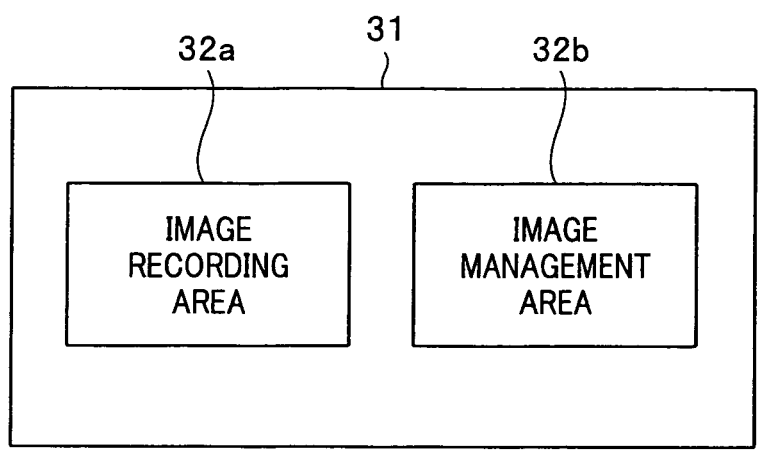
FIG. 18 is an explanatory view for describing recording areas of an internal HDD 31.

FIG. 18 is an explanatory view for describing recording areas of the internal HDD 31. The internal HDD 31 includes an image management area 32*b* that is outside an image recording area 32*a*. Medical images such as moving images and still images and the like are recorded in the image recording area 32*a* of the internal HDD 31. An image that is recorded in the image recording area 32*a* in the internal HDD 31 can be written to the external medium 51 through the reading portion 302 by the recorded information management portion 301 in accordance with a user operation. In the present embodiment, management information relating to recording and the like of image data that is recorded in the image recording area 32*a* and is written to the external medium 51 is recorded as the database 31*a* in the image management area 32*b*.

FIG. 19 is an explanatory view that illustrates a management table that is one example of management information that is recorded as the database 31*a*.

As shown in FIG. 19, the management table includes an internal HDD management table for managing images that are recorded on the internal HDD 31, and an external media management table for managing the external medium 51 on which images have been written.

As shown in FIG. 19, the information in the internal HDD management table includes an ID for identifying a patient, a patient name, a date, a file management number (No.) that is associated with an image recorded in the image recording area 32*a*, and a flag indicating whether or not an image exists in the image recording area 32a. The flag is "1" in a case where an image is written in the image recording area 32a of the internal HDD 31, and is "0" in a case where the relevant image was deleted from the image recording area 32a. The recorded information management portion 301 acquires these items of information from the control portion 28 and generates the management table.

The external media management table includes information regarding "write medium type" that shows the type of external medium on which an image is to be recorded when writing an image, and "serial No. of medium" that records information for identifying a medium on which the image is to be recorded.

A volume name is used as the medium serial number when the external medium 51 is an optical disk such as a Blue-ray disk or a digital versatile disk, and a serial number is used as the medium serial number when the external medium 51 is a USB storage such as a USB memory or a USB-HDD, or a semiconductor memory such as an SD card. The recorded information management portion 301 acquires these items of information from the external medium 51 through the reading portion 302 and generates the management table.

Note that an NAS (network attached storage) or a storage server or the like may also be adopted as an external medium. In this case, the recorded information management portion 301 may record the server name as the medium serial number.

When writing an image onto the external medium 51, the recorded information management portion 301 is configured to create a folder name using values for the ID and date in the internal HDD management table, and write the image file in the created folder. Note that the name of the image file in this case is created, for example, by means of the folder name and file management number.

For example, for the record indicated by file management number 1 in FIG. 19, the folder name will be "1234567_2010_02_16", and the file name will be "1234567_2010_02_16_h-1234567-1.mp4".

The recorded information management portion 301 can read out the contents of the database 31a constructed in the image management area 32b, and output the contents to the data processing portion 303 through the reading portion 302. The data processing portion 303 can convert the management table to a form that can be displayed on the monitor 40 and output the management table in the converted form. It is thereby possible to cause the contents of the management table to be displayed on the monitor 40 by a menu operation or the like performed by the user.

Figure 20:
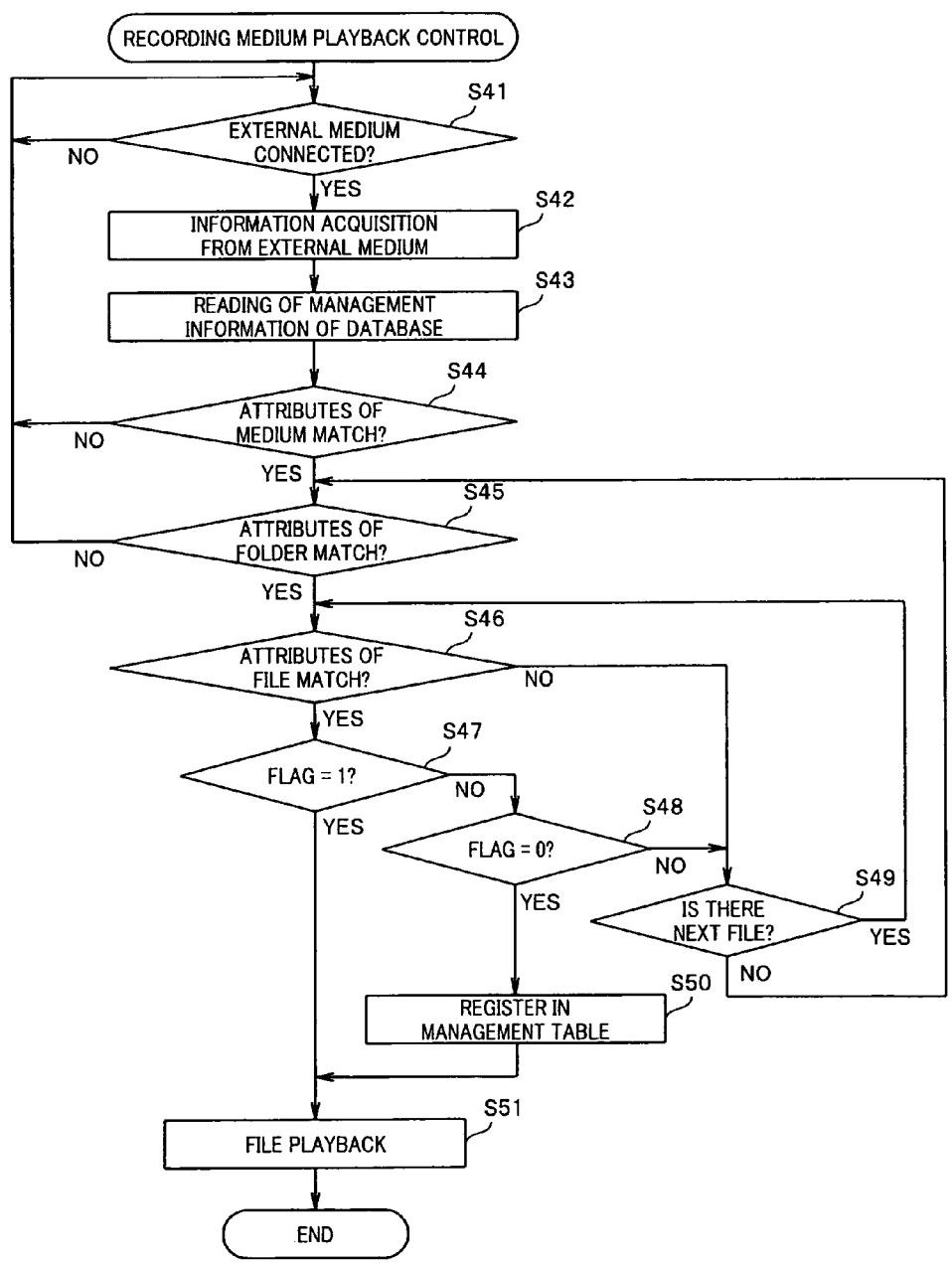
FIG. 20 is a flowchart for describing playback control of a recording medium.

Next, operations of the embodiment configured in this manner will be described referring to FIG. 20. FIG. 20 is a flowchart for describing playback control of a recording medium.

The processing to record a medical image onto the internal HDD 31 is the same as in the first embodiment. In the present embodiment, when writing a medical image that is recorded on the internal HDD 31 onto the external medium 51, a management table is generated by the recorded information management portion 301.

For example, when writing of an image to the external medium 51 is instructed by a user operation of the input apparatus 11, the recorded information management portion 301 is controlled by the control portion 28 to read the relevant image from the image recording area 32a in the internal HDD 31 and supply the image to the reading portion 302. The reading portion 302 provides the image data that is read from the recorded information management portion 301 to the external medium 51 to record the image data thereon.

When writing the image data, information relating to the read image is provided from the control portion 28 to the recorded information management portion 301, and the recorded information management portion 301 creates an internal HDD management table. Further, the recorded information management portion 301 reads the type and volume label of the external medium 51 and records the type and volume label in the columns for write medium type and medium serial No., respectively, in the external media management table. In this way, the respective records shown in FIG. 19 are generated for each image that is written. Note that with respect to a record relating to an image that was deleted from the internal HDD 31 among the respective records of the management table, the recorded information management portion 301 changes the flag of the relevant record from "1" to "0" and does not delete the record from the management table.

Next, operations are described for a case in which the external medium 51 that was detached once from the medical information recording apparatus 300 is reattached thereto and an image that is recorded on the external medium 51 is read and displayed on the monitor 40.

In step S41 in FIG. 20, the recorded information management portion 301 determines whether or not the external medium 51 is connected based on information from the reading portion 302. If the external medium 51 is connected, the recorded information management portion 301 reads information relating to the external medium 51 through the reading portion 302 (step S42). The recorded information management portion 301 also reads information of the management table in the database 31a (step S43).

Next, the recorded information management portion 301 performs a check regarding whether or not the external medium 51 from which reading is to be performed is a medium on which a medical image from the internal HDD 31 was recorded. That is, in step S44 the recorded information management portion 301 determines whether or not a record having a medium type and a medium serial number that is the same as the medium type and medium serial number acquired from the external medium 51 exists in the management table. If the same medium type and medium serial number exist, the recorded information management portion 301 determines that the external medium 51 is a medium on which a medical image from the internal HDD 31 was recorded, and performs the determination in the subsequent step S45.

In step S45, with respect to a file to be read from the external medium 51, the recorded information management portion 301 determines whether or not an ID and date that indicate a folder name in which the file is stored match a record (ID and date) in the management table. If the ID and date match a record in the management table, next, in step S46, the recorded information management portion 301 determines whether or not the file name of the file to be read from the external medium 51 matches a record (file management number) in the management table. If the file name matches the record, thereafter, in step S47, the recorded information management portion 301 determines whether or not the flag is "1". Further, in step S48, the recorded information management portion 301 determines whether or not the flag is "0".

Regardless of whether the flag is "1" or "0", if it is determined in step S46 that a file that matches a record in the management table of the database 31a exists in the external medium 51, in step S51 the recorded information management portion 301 permits playback of the relevant file in the external medium 51.

The recorded information management portion 301 controls the reading portion 302 in accordance with an instruction of the control portion 28 to read a file specified by the user and supply the file to the data processing portion 303. The data processing portion 303 expands the read data into a video signal, and thereafter provides the video signal to the monitor 40 through the I/F 304. For example, the data processing portion 303 may cause the monitor 40 to display the medical image in the original size thereof or to display the medical image as a thumbnail image. Thus, a medical image or the like that is recorded on the external medium 51 can be displayed.

In contrast, if it is determined in step S46 that a file that matches a record in the management table of the database 31a does not exist on the external medium 51, the recorded information management portion 301 does not permit playback of the relevant file in the external medium 51. By performing step S49 to confirm whether there is a next file and, based on the result, returning the process to step S45 or S46, for all of the files in the folder, the recorded information management portion 301 checks whether or not a record for the same file exists in the management table.

A flag of a file that is recorded on the external medium 51 and that has been deleted from the internal HDD 31 is "0" in the management table. When such a file exists, the recorded information management portion 301 shifts the process from step S48 to step S50, and registers information relating to the relevant file in the management table. For example, in a case where an image file that is managed as a file whose flag is "0" in the management table is read from an external medium, together with reading and playing back the file, the recorded information management portion 301 constructs a read table based on which the history is known, and registers a link for the image file in the table. Thus, in a case where the image file is played back often, the image file can be read immediately without executing the processing flow in FIG. 20 each time.

Thus, according to the present embodiment, in a case where a medical image is recorded on an external medium and thereafter the external medium on which the medical image is recorded is reconnected to the present recording apparatus, a management table is used to check whether or not the external medium is the external medium that was used when recording the medical image, and a check is also performed regarding whether or not a file exists thereon that matches a file in the management table to thereby determine whether or not to permit playback of the relevant file. Thus, according to the present embodiment, an image recorded on an external medium can be played back and displayed while ensuring security, thereby providing excellent convenience for the user.

Note that the present invention is not limited to the precise embodiments described above, and can be embodied in the implementing stage by modifying the components without departing from the scope of the invention. Also, various inventions can be formed by appropriately combining a plurality of the components disclosed in the respective embodiments described above. For example, some components may be deleted from all of the disclosed components according to the embodiments. Furthermore, components from different embodiments may be appropriately combined.

What is claimed is:

1. A medical information recording apparatus, comprising:
an input portion having a plurality of input terminals and into which one or more medical images are inputted from a plurality of image pickup apparatuses, the input portion being configured to detect whether the medical image is inputted through any input terminal among the plurality of input terminals and to output the detection result;
a screen synthesis portion configured to: (i) determine a content of a medical scene based on the detection result of the input portion, (ii) select one synthesis pattern corresponding to the medical scene from a predefined plurality of synthesis patterns based on the determined medical scene, (iii) perform synthesis processing in accordance with the selected synthesis pattern with respect to the inputted one or more medical images inputted through the plurality of input terminals, and (iv) output a synthesized image generated by the synthesis processing based on the inputted one or more medical images and the selected synthesis pattern, the screen s synthesis portion including:
an image analysis portion configured to analyze the content of the one or more inputted medical images, and
a synthesis pattern decision portion configured to select a synthesis pattern for the synthesis processing based on the analyzed content of the one or more inputted medical images; and
a recording processing portion configured to record the synthesized image as a single image file, wherein:
the image analysis portion outputs a result of analysis of a color distribution of an image; and
based on the color distribution, the synthesis pattern decision portion selects a synthesis pattern for the synthesis processing.

2. A medical information recording apparatus, comprising:
an input portion having a plurality of input terminals and into which one or more medical images are inputted from a plurality of image pickup apparatuses, the input portion being configured to detect whether the medical image is inputted through any input terminal among the plurality of input terminals and to output the detection result;
a screen synthesis portion configured to: (i) determine a content of a medical scene based on the detection result of the input portion, (ii) select one synthesis pattern corresponding to the medical scene from a predefined plurality of synthesis patterns based on the determined medical scene, (iii) perform synthesis processing in accordance with the selected synthesis pattern with respect to the inputted one or more medical images inputted through the plurality of input terminals, and (iv) output a synthesized image generated by the synthesis processing based on the inputted one or more medical images and the selected synthesis pattern, the screen synthesis portion including:
an image analysis portion configured to analyze the content of the one or more inputted medical images, and
a synthesis pattern decision portion configured to select a synthesis pattern for the synthesis processing based on the analyzed content of the one or more inputted medical images; and
a recording processing portion configured to record the synthesized image as a single image file, wherein:
the image analysis portion outputs a result of analysis of a contour of a picture in an image; and
based on the contour, the synthesis pattern decision portion selects a synthesis pattern for the synthesis processing.

3. A medical information recording apparatus, comprising:
an input portion having a plurality of input terminals and into which one or more medical images are inputted from a plurality of image pickup apparatuses, the input portion being configured to detect whether the one or more medical images are inputted through an input terminal among the plurality of input terminals and to output the detection result;

a screen synthesis portion configured to: (i) determine a content of a medical scene based on the detection result of the input portion and an image analysis result with respect to one or more of the medical images inputted through the plurality of input terminals, (ii) select one synthesis pattern from a predefined plurality of synthesis patterns based on: (a) the determined medical scene, and (b) the image analysis result, (iii) perform synthesis processing in accordance with the selected synthesis pattern with respect to one or more of the medical images inputted through the plurality of input terminals, and (iv) output a synthesized image generated by the synthesis processing based on the inputted one or more medical images and the selected synthesis pattern, the screen synthesis portion including:

an image analysis portion configured to analyze the content of the one or more inputted medical images, and a synthesis pattern decision portion configured to select a synthesis pattern for the synthesis processing based on the analyzed content of the one or more inputted medical images; and a recording processing portion configured to record the synthesized image as a single image file, wherein:

the image analysis portion outputs a result of analysis of a color distribution of an image; and based on the color distribution, the synthesis pattern decision portion selects a synthesis pattern for the synthesis processing.

4. A medical information recording apparatus, comprising:

an input portion having a plurality of input terminals and into which one or more medical images are inputted from a plurality of image pickup apparatuses, the input portion being configured to detect whether the one or more medical images are inputted through any input terminal among the plurality of input terminals and to output the detection result;

a screen synthesis portion configured to: (i) determine a content of a medical scene based on the detection result of the input portion and an image analysis result with respect to one or more of the medical images inputted through the plurality of input terminals, (ii) select one synthesis pattern from a predefined plurality of synthesis patterns based on: (a) the determined medical scene, and (b) the image analysis result, (iii) perform synthesis processing in accordance with the selected synthesis pattern with respect to one or more of the medical images inputted through the plurality of input terminals, and (iv) output a synthesized image generated by the synthesis processing based on the inputted one or more medical images and the selected synthesis pattern, the screen synthesis portion including:

an image analysis portion configured to analyze the content of the one or more inputted medical images, and a synthesis pattern decision portion configured to select a synthesis pattern for the synthesis processing based on the analyzed content of the one or more inputted medical images; and a recording processing portion configured to record the synthesized image as a single image file, wherein:

the image analysis portion outputs a result of analysis of a contour of a picture in an image; and based on the contour, the synthesis pattern decision portion selects a synthesis pattern for the synthesis processing.

* * * * *